(12) United States Patent
Shin et al.

(10) Patent No.: US 10,240,129 B2
(45) Date of Patent: Mar. 26, 2019

(54) BACTERIOPHAGE AND COMPOSITION COMPRISING SAME

(71) Applicant: CJ CHEILJEDANG CORPORATION, Seoul (KR)

(72) Inventors: Eun Mi Shin, Seoul (KR); Gi Duk Bae, Seoul (KR); Jae Won Kim, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 127 days.

(21) Appl. No.: 15/304,402

(22) PCT Filed: Apr. 14, 2015

(86) PCT No.: PCT/KR2015/003705
§ 371 (c)(1),
(2) Date: Oct. 14, 2016

(87) PCT Pub. No.: WO2015/160165
PCT Pub. Date: Oct. 22, 2015

(65) Prior Publication Data
US 2017/0037382 A1    Feb. 9, 2017

(30) Foreign Application Priority Data

Apr. 15, 2014 (KR) .................. 10-2014-0044997

(51) Int. Cl.
| | | |
|---|---|---|
| *C12N 7/00* | (2006.01) | |
| *A23K 10/18* | (2016.01) | |
| *A23K 20/195* | (2016.01) | |
| *A23K 50/70* | (2016.01) | |
| *A23K 50/75* | (2016.01) | |
| *A23K 20/153* | (2016.01) | |
| *A61K 35/76* | (2015.01) | |

(52) U.S. Cl.
CPC .............. *C12N 7/00* (2013.01); *A23K 10/18* (2016.05); *A23K 20/153* (2016.05); *A23K 20/195* (2016.05); *A23K 50/70* (2016.05); *A23K 50/75* (2016.05); *A61K 35/76* (2013.01); *C12N 2795/00021* (2013.01); *C12N 2795/00032* (2013.01); *C12N 2795/10121* (2013.01); *C12N 2795/10132* (2013.01)

(58) Field of Classification Search
None
See application file for complete search history.

(56) References Cited

U.S. PATENT DOCUMENTS 9,938,506 B2 *  4/2018  Seo ..................... A23K 50/75

FOREIGN PATENT DOCUMENTS

| JP | 2011-509653 A | 3/2011 |
|---|---|---|
| KR | 10-2012-0111535 A | 10/2012 |
| KR | 10-1299179 B1 | 8/2013 |
| KR | 10-1381793 B1 | 4/2014 |

OTHER PUBLICATIONS

KR 10-1299179 (CJ Cheiljedang Corporation, 2013), machine translation.*
International Search Report dated Jul. 15, 2015 of PCT/KR2015/003705 which is the parent application and its English translation—4 pages.
Extended European Search Report dated Aug. 3, 2017 of corresponding European Patent Application No. 15779395.1—9 pages.
Huff et al., "Method of administration affects the ability of bacteriophage to prevent colibacillosis in 1-day-old broiler chickens", Poultry Science, vol. 92, No. 4, Apr. 2013, pp. 930-934.
Lau et al., "Efficacy of a bacteriophage isolated from chickens as a therapeutic agent for colibacillosis in broiler chickens", Poultry Science, vol. 89, No. 12, Dec. 2010, pp. 2589-2596.
Oliveira et al., "In vivo efficiency evaluation of a phage cocktail in controlling severe colibacillosis in confined conditions and experimental poultry houses", Veterinary Microbiology, vol. 146, No. 3-4, Dec. 2010, pp. 303-308.
Tsonos et al., "A cocktail of in vitro efficient phages is not a guarantee for in vivo therapeutic results against avian colibacillosis", Veterinary Microbiology, vol. 171, No. 3-4, Jul. 2014, pp. 470-479.
Li et al., "Complete Genome Sequence of the Novel Lytic Avian Pathogenic Coliphage NJ01", Journal of Virology, vol. 36, No. 24—2 pp. (Dec. 2012).
Office Action and Search Report of corresponding Chinese Patent Application No. 2015800320483—6 pages (Jan. 22, 2019).

* cited by examiner

*Primary Examiner* — Irene Marx
(74) *Attorney, Agent, or Firm* — Knobbe Martens Olson & Bear LLP

(57) ABSTRACT

The present invention relates to a novel bacteriophage ΦCJ25 (KCCM11463P) and a composition comprising the same as an active ingredient. In addition, the present invention relates to a method for preventing and/or treating infectious diseases caused by avian pathogenic *Escherichia coli* (APEC) of birds by using the bacteriophage ΦCJ25 (KCCM11463P) or the composition.

3 Claims, 3 Drawing Sheets

Specification includes a Sequence Listing.

[Fig. 1]
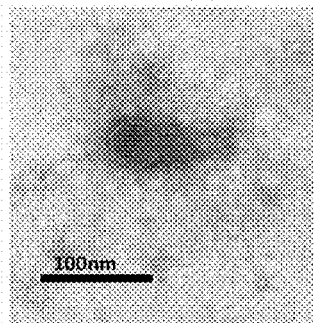
[Fig. 2]
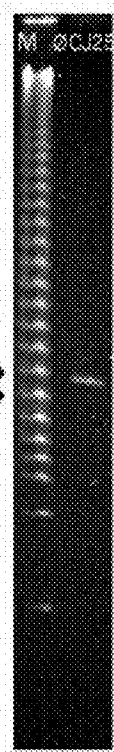

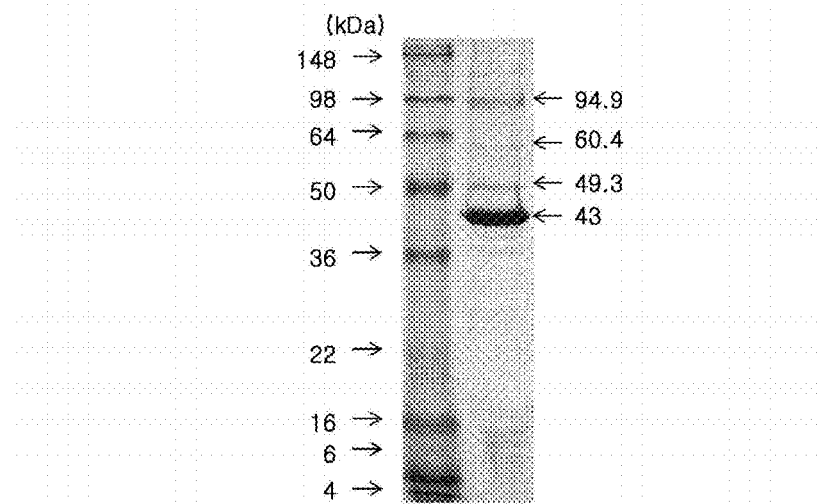
[Fig. 3]
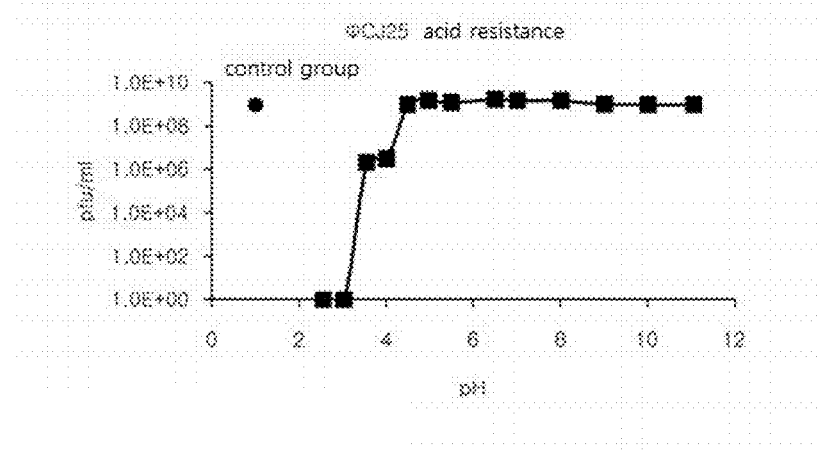
[Fig. 4]

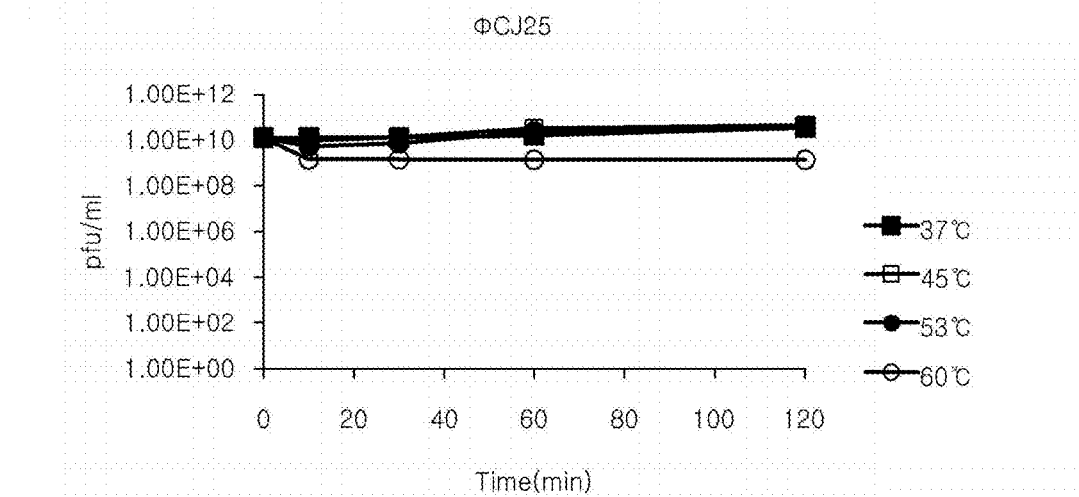
[Fig. 5]
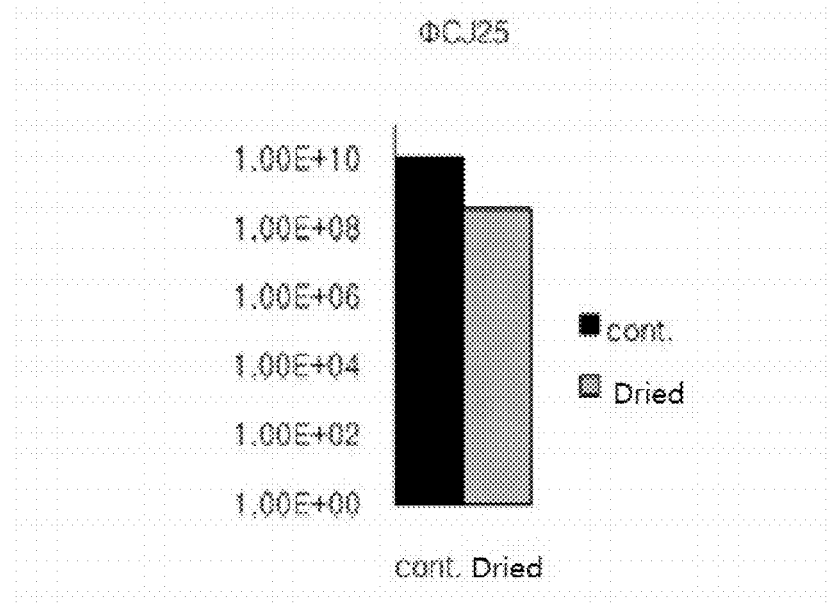
[Fig. 6]

BACTERIOPHAGE AND COMPOSITION COMPRISING SAME

TECHNICAL FIELD

The present invention relates to a novel bacteriophage having a specific ability to kill avian pathogenic *Escherichia coli* (APEC), a composition including the same, and a method for preventing or treating infectious diseases of birds using the novel bacteriophage or the composition.

BACKGROUND ART

*Escherichia coli* (hereinafter also referred to as *E. coli*) is a Gram-negative, short rod bacterium of genus *Escherichia*, family Enterobacteriaceae, and one of normal flora found in intestines of various animals including mammals. Most strains of *Escherichia coli* are non-pathogenic and can cause opportunistic infection, but some highly pathogenic strains cause various intestinal diseases and sepsis in animals including humans.

Among these strains of *Escherichia coli*, avian pathogenic *E. coli* causes infection through the respiratory tract of birds such as chickens, geese, turkeys, and the like, and is known to pass into the avian body through the respiratory mucous membrane. Avian pathogenic *E. coli* causes diseases mostly in poultry with respect to respiratory diseases in birds, which leads to enormous economic damage in the poultry industry.

Meanwhile, a bacteriophage refers to a bacterium specific virus that prevents and inhibits growth of a bacterium infected with a specific bacteriophage. As bacteriophages have stronger host specificity than antibiotics, and recent emergence of bacteria resistant to antibiotics and residual antibiotics in animals are growing problems, application of bacteriophages has drawn great interest.

Studies on bacteriophages have been actively performed in many countries, and there has been an increasing tendency to obtain approval from the Food and Drug Administration (FDA) for compositions using bacteriophages in addition to patent applications for bacteriophages.

However, bacteriophage related technologies for prevention and/or treatment of infectious diseases, which are important issues in the aviculture industry including poultry farming, due to avian pathogenic *Escherichia coli* are still insufficient, and therefore, there is a need for such bacteriophages and development of relevant technologies.

DISCLOSURE

Technical Problem

As a result of earnest investigation aimed at overcoming the emergence of bacteria resistant to antibiotics and residual antibiotics in animals and at effectively preventing and treating infectious diseases of birds, the present inventors isolated a novel bacteriophage ΦCJ25 (KCCM11463P) having a specific ability to kill avian pathogenic *Escherichia coli* causing respiratory diseases of poultry from natural sources.

In addition, the present inventors identified morphological, biochemical, and genetic properties of the novel bacteriophage, confirmed that the bacteriophage has excellent acid resistance, heat resistance, and drying resistance, and developed antibiotics, disinfectants, additives for feeds, and other compositions using the bacteriophage, a composition for preventing or treating infectious diseases in birds, and a method for preventing or treating diseases using the same.

It is an object of the present invention to provide a novel bacteriophage ΦCJ25 (KCCM11463P) having a specific ability to kill avian pathogenic *Escherichia coli*.

It is another object of the present invention to provide a composition for preventing and/or treating infectious diseases caused by avian pathogenic *Escherichia coli*, including the bacteriophage ΦCJ25 (KCCM11463P) as an active ingredient.

It is a further object of the present invention to provide antibiotics, additives for feeds, additives for drinking water, feeds, drinking water, disinfectants or detergents, including the bacteriophage ΦCJ25 (KCCM11463P) as an active ingredient.

It is yet another object of the present invention to provide a method for preventing and/or treating infectious diseases caused by avian pathogenic *Escherichia coli* using the bacteriophage ΦCJ25 (KCCM11463P) or the composition including the bacteriophage ΦCJ25 (KCCM11463P) as an active ingredient.

Technical Solution

One aspect of the present invention provides a novel bacteriophage ΦCJ25 (KCCM11463P) having a specific ability to kill avian pathogenic *Escherichia coli*.

Another aspect of the present invention provides a composition for preventing or treating infectious diseases caused by avian pathogenic *Escherichia coli*I, including the bacteriophage ΦCJ25 (KCCM11463P) as an active ingredient.

A further aspect of the present invention provides antibiotics, additives for feeds, additives for drinking water, feeds, drinking water, disinfectants or detergents, including the bacteriophage ΦCJ25 (KCCM11463P) as an active ingredient.

Yet another aspect of the present invention provides a method for preventing or treating infectious diseases caused by avian pathogenic *Escherichia coli*, including: administering the bacteriophage ΦCJ25 (KCCM11463P) or the composition including the bacteriophage ΦCJ25 (KCCM11463P) as an active ingredient to birds.

Advantageous Effects

The bacteriophage ΦCJ25 (KCCM11463P) according to the present invention has an effect of having a specific ability to kill avian pathogenic *Escherichia coli*.

Further, the bacteriophage ΦCJ25 (KCCM11463P) according to the present invention has excellent acid resistance, heat resistance, and drying resistance, and thus can be employed not only as an agent for preventing or treating infectious diseases caused by avian pathogenic *Escherichia coli* at various ranges of temperature, pH, and dry conditions but also as antibiotics, additives for feeds, additives for drinking water, feeds, drinking water, disinfectants, detergents, and the like, including the bacteriophage ΦCJ25 (KCCM11463P) as an active component.

Further, the present invention provides the bacteriophage ΦCJ25 (KCCM11463P) or antibiotics including the same as an active ingredient, and the antibiotics have effects in that the antibiotics have specificity for avian pathogenic *Escherichia coli* as compared to prior antibiotics and thus selectively kill specific pathogenic bacteria without killing beneficial bacteria; and that the antibiotics do not induce drug resistance, resulting in extension of lifetime of products as compared to prior antibiotics.

Further, the present invention has effects of preventing or treating infectious diseases caused by avian pathogenic

*Escherichia coli* by administering the bacteriophage ΦCJ25 (KCCM11463P) or the composition including the bacteriophage ΦCJ25 (KCCM11463P) as an active ingredient to birds.

DESCRIPTION OF DRAWINGS

FIG. 1 is an electron microscope image of a novel bacteriophage ΦCJ25 (KCCM11463P) (hereinafter referred to as 'ΦCJ25').

FIG. 2 shows results of pulsed field gel electrophoresis (PFGE) of a novel bacteriophage ΦCJ25.

FIG. 3 shows results of sodium dodecyl sulfate polyacrylamide gel electrophoresis (SDS-PAGE) of a novel bacteriophage ΦCJ25.

FIG. 4 is a graph depicting results of acid resistance experiment of a novel bacteriophage ΦCJ25.

FIG. 5 is a graph depicting results of heat resistance experiment of a novel bacteriophage ΦCJ25.

FIG. 6 is a graph depicting results of drying resistance experiment of a novel bacteriophage ΦCJ25.

EMBODIMENTS

Hereinafter, embodiments of the present invention will be described in more detail. Description of details apparent to a person having ordinary knowledge in the art will be omitted herein.

One embodiment of the present invention provides a novel bacteriophage ΦCJ25 (KCCM11463P) (hereinafter referred to as 'ΦCJ25') having a specific ability to kill avian pathogenic *Escherichia coli* (APEC).

Avian pathogenic *Escherichia coli* refers to *Escherichia coli* that is transmitted through the respiratory tract of birds such as chickens, geese, turkeys, and the like, and that can cause infectious diseases of birds, specifically avian colibacillosis. Specifically, avian pathogenic *Escherichia coli* penetrates into the body of birds through the mucous membrane of the respiratory tract, and causes various diseases such as sepsis, granuloma, air sacculitis, salpingitis, arthritis, and the like. Avian pathogenic *Escherichia coli* is a Gramnegative *bacillus* just like general *Escherichia coli*, has peritrichous flagella for motility, and is an aerobic or facultative anaerobic bacterium which decomposes lactose and fructose to generate acids and gases.

Avian pathogenic *Escherichia coli* grows well on common media and is capable of growing at a temperature of about 7° C. to about 48° C. with ideal growth temperature ranging from about 35° C. to about 37° C. Specifically, at around 42° C. which is close to body temperature of birds, expression of pathogenic factors is effectively performed. Further, avian pathogenic *Escherichia coli* can grow at pH ranging from pH 4.5 to pH 9.0.

A bacteriophage is a bacteria-specific virus capable of infecting a specific bacterium and inhibiting growth of the bacterium, and is a virus including single or double-stranded deoxyribonucleic acid (DNA) or ribonucleic acid (RNA) as a genetic material.

Specifically, the bacteriophage ΦCJ25 according to the embodiment of the present invention is a bacteriophage that has species specificity of selectively infecting avian pathogenic *Escherichia coli* and morphologically belongs to *Myoviridae* having an icosahedral capsid and a contractile tail (see FIG. 1). Homology between a nucleotide sequence of the bacteriophage ΦCJ25 and decoded nucleotide sequences of other bacteriophages is compared and results are shown in Table 1. The bacteriophage ΦCJ25 shows stable acid resistance at pH 3.5 to pH 11.0 without losing activity (FIG. 4), and in terms of heat resistance, the bacteriophage ΦCJ25 does not show activity decline even when exposed to 50° C. or more (for example, 53° C.) for two hours (FIG. 5). In terms of drying resistance, the bacteriophage ΦCJ25 shows activity decline of about 2 log after drying (FIG. 6). DNA nucleotide sequence of the bacteriophage ΦCJ25 is set forth in SEQ ID NO: 1 of Sequence List.

The bacteriophage ΦCJ25 is a novel bacteriophage isolated by the present inventor, and was deposited at the Korean Culture Center of Microorganisms (KCCM) (361-221, Hongje 1-dong, Seodaemun-gu, Seoul, Korea) on Oct. 25, 2013 under accession number KCCM 11462P.

Another embodiment of the present invention provides a composition for preventing or treating infectious diseases caused by avian pathogenic *Escherichia coli*, including the bacteriophage ΦCJ25 as an active ingredient.

Since the bacteriophage ΦCJ25 exhibits antibacterial activity capable of specifically killing avian pathogenic *Escherichia coli*, the bacteriophage ΦCJ25 can be utilized in prevention or treatment of diseases caused by infection with avian pathogenic *Escherichia coli*. Examples of infectious diseases caused by avian pathogenic *Escherichia coli* include avian colibacillosis, without being limited thereto.

Herein, the term "avian colibacillosis" refers to a disease occurring in the respiratory tract of birds due to infection with pathogenic *Escherichia coli*, and symptoms thereof include air sacculitis, perihepatitis, peritonitis, pericarditis, salpingitis, omphalitis, osteomyelitis or septicemia, thereby causing growth delay and mortality of infected birds.

Herein, the term "preventing" or "prevention" refers to all actions to inhibit the diseases or delay occurrence of the diseases by administering the bacteriophage ΦCJ25 and/or the composition including the bacteriophage ΦCJ25 as an active ingredient to an animal.

Herein, the term "treating" or "treatment" refers to all actions to improve or ameliorate symptoms of infectious diseases by administering the bacteriophage ΦCJ25 and/or the composition including the bacteriophage ΦCJ25 as an active ingredient to an animal.

The composition for preventing or treating infectious diseases caused by avian pathogenic *Escherichia coli* according to this embodiment may include the bacteriophage ΦCJ25 in amounts of $5 \times 10^2$ pfu/ml to $5 \times 10^{12}$ pfu/ml, specifically, $1 \times 10^6$ pfu/ml to $1 \times 10^{10}$ pfu/ml.

The composition for preventing or treating infectious diseases caused by avian pathogenic *Escherichia coli* according to this embodiment may further include pharmaceutically acceptable carriers, and may be formulated with the carriers to provide foods, medicines, additives for feeds or additives for drinking water, and the like.

Herein, the term "pharmaceutically acceptable carriers" refers to carriers or diluents that do not stimulate an organism and do not inhibit biological activity and properties of administered compounds.

Types of carriers applicable to this embodiment are not particularly limited and any pharmaceutically acceptable carriers commonly used in the art may be utilized. Examples of the carriers may include saline, distilled water, Ringer's solution, buffered saline, an albumin injection solution, a dextrose solution, a maltodextrin solution, glycerol, and ethanol, without being limited thereto. These may be used alone or in combination thereof.

Furthermore, as needed, other common additives such as antioxidants, buffered solutions and/or cytostatics may be added to the composition according to the present invention, and diluents, dispersants, surfactants, binders and/or lubricants may be further added to the composition according to the present invention to formulate injectable formulations such as aqueous solutions, suspensions and emulsions, pills, capsules, granules, and tablets.

Methods for administering the composition for preventing or treating infectious diseases caused by avian pathogenic *Escherichia coli* according to this embodiment are not particularly limited, and any methods commonly used in the related art may be used. One example of the administration method may include oral administration or parenteral administration.

Examples of dosage forms for oral administration may include troches, lozenges, tablets, water soluble suspensions, oil-based suspensions, formulated powder, granules, emulsions, hard capsules, soft capsules, syrups, and elixirs.

In order to formulate the composition according to this embodiment into dosage forms such as tablets or capsules, binders such as lactose, saccharose, sorbitol, mannitol, starches, amylopectin, cellulose and gelatin; excipients such as dicalcium phosphate; disintegrators such as corn starch and sweet potato starch; lubricants such as magnesium stearate, calcium stearate, sodium stearyl fumarate and polyethylene glycol wax may be further included, and for capsule formulation, liquid carriers such as fatty oils may be further included in addition to the aforementioned substances.

Methods for parenterally administering the composition of this embodiment may include, for example, intravenous injection, intraperitoneal administration, intramuscular administration, subcutaneous administration, and topical administration, and a method of applying or spraying the composition according to the present invention to an affected region, without being limited thereto.

In order to formulate parenteral dosage forms, for example, the composition of this embodiment may be formulated into dosage forms for injection such as subcutaneous injection, intravenous injection and intramuscular injection; suppositories; or dosage forms for spraying such as aerosols so as to permit inhalation through inhalers, without being limited thereto. In order to formulate dosage forms for injection, the composition of this embodiment may be mixed with stabilizers or buffering agents in water to prepare solutions or suspensions, which are formulated into dosage forms for unit administration such as ampoules or vials. When the composition is formulated into dosage forms for spraying such as aerosols, the composition may be formulated with propellants and the like together with additives such that a concentrate dispersed in water or wetted powder is dispersed therein.

Suitable amounts of applying, spraying or administering the composition for preventing or treating infectious diseases caused by avian pathogenic *Escherichia coli* according to this embodiment may differ according to factors such as age, body weight and sex of animals, degree of disease symptoms, ingested foods, rate of excretion, and the like in addition to a method for formulating the composition, an administration method, administration time and/or routes for administration, and a generally skilled veterinarian can easily determine and prescribe dose amounts effective for intended treatment.

A further embodiment of the present invention provides antibiotics including the bacteriophage ΦCJ25 as an active ingredient.

Herein, the term "antibiotics" refers to a preparation that is administered to animals including humans in medicine form and exhibits efficacy of sterilizing bacteria, and is used as a general term for antiseptics, germicides and antibacterial agents.

Antibiotics of this embodiment including the bacteriophage ΦCJ25 as an active ingredient have effects in that the antibiotics have specificity for avian pathogenic *Escherichia coli* as compared to typical antibiotics and thus kill specific pathogenic bacteria, but not beneficial bacteria; and in that the antibiotics do not induce antibiotic resistance, causing extension of lifetime of products as compared to typical antibiotics.

Yet another embodiment of the present invention provides an additive for avian feeds or avian drinking water, which includes the bacteriophage ΦCJ25 as an active ingredient.

Birds as a subject to which the additives for avian feeds or the additives for avian drinking water are applied are not particularly limited, but birds in this embodiment are particularly poultry.

Herein, poultry is a generic name for animals belonging to birds among livestock. Poultry is not particularly limited, and may comprise at least one selected from the group consisting of chickens, geese, turkeys, and the like.

The additives for avian feeds or the additives for avian drinking water may be used by separately preparing additives for feeds or additives for avian drinking water using the bacteriophage ΦCJ25 or the composition including the same and mixing feeds or drinking water with the additives, or directly adding the bacteriophage ΦCJ25 or the composition including the same in a process of preparing feeds or drinking water.

The bacteriophage ΦCJ25 or the composition including the bacteriophage ΦCJ25 as an active ingredient used in the form of additives for feeds or additives for drinking water according to this embodiment may be a liquid form or a dried form, for example, a dried powder form.

For example, the bacteriophage ΦCJ25 according to the present invention is mixed in powder form in amounts of 0.05% by weight (wt %) to 10 wt %, specifically 0.1 wt % to 2 wt %, based on the weight of additives for feeds.

Methods for drying the additives for feeds or additives for drinking water according to this embodiment to yield dried powder are not particularly limited, and any methods commonly used in the related art may be utilized. Examples of the drying method may include air drying, natural drying, spray drying, and lyophilization, without being limited thereto. These methods may be used alone or in combination thereof.

The additives for feeds or additives for drinking water according to this embodiment may further include other non-pathogenic microorganisms. The microorganisms may be selected from the group consisting of *Bacillus* sp. such as *Bacillus subtilis* capable of producing proteases, lipases and/or glycosyltransferases; lactic acid bacteria such as *Lactobacillus* sp. having physiological activity and organic material decomposing capability under anaerobic conditions like the stomach of cattle; filamentous bacteria such as *Aspergillus oryzae* having effects of weight gain in animals, increase in milk production, and increase of digestion-absorption rate of feeds; and yeasts such as *Saccharomyces cerevisiae* and the like. These microorganisms may be used alone or in combination thereof.

The additives for feeds or additives for drinking water according to this embodiment including the bacteriophage ΦCJ25 as an active ingredient may further include other additives as needed. Examples of usable additives may include binders, emulsifiers, and preservatives added for prevention of quality deterioration of feeds or drinking water; amino acid, vitamin, enzyme, probiotics, flavoring agents, non-protein nitrogen compounds, silicate, buffering agents, coloring agents, extracting agents or oligosaccharides that are added in order to increase utility of feeds or drinking water; and other supplements to feeds, and the like. These additives may be used alone or in combination thereof.

The additives for feeds according to the present invention may be present in amounts of 0.05 parts by weight to 10 parts by weigh, specifically 0.1 parts by weight to 2 parts by weight, based on 100 parts by weight of feeds. The additives for drinking water according to the present invention may be present in amounts of 0.0001 parts by weight to 0.01 parts by weight, specifically 0.001 parts by weight to 0.005 parts by weight, based on 100 parts by weight of drinking water. Within these ranges, the additives allow activity of the bacteriophage ΦCJ25 against avian pathogenic *Escherichia coli* to be sufficiently displayed.

Yet another embodiment of the present invention provides feeds or drinking water prepared by adding the additives for feeds or the additives for drinking water including the bacteriophage ΦCJ25 as an active ingredient to feeds or drinking water, or directly adding the bacteriophage ΦCJ25 thereto.

Feeds used in this embodiment are not particularly limited, and any feeds commonly used in the related art may be used. Examples of the feeds may include vegetable feeds such as grains, root vegetables, food processing byproducts, algae, fibers, pharmaceutical byproducts, oils and fats, starches, residues or byproducts of grain, and the like; and animal feeds such as proteins, inorganic substances, oils and fats, minerals, single cell proteins, and animal planktons or foods. These feeds are used alone or in combination thereof.

Drinking water used in this embodiment is not particularly limited, and any drinking water commonly used in the related art may be used.

Yet another embodiment of the present invention provides disinfectants or detergents including the bacteriophage ΦCJ25 as an active ingredient. Dosage forms of the disinfectants or detergents are not particularly limited, and any dosage forms commonly used in the related art may be used.

In order to remove avian pathogenic *Escherichia coli*, the disinfectants may be sprayed to habitats of birds, slaughterhouses, dead regions, kitchens, and cooking equipment, without being limited thereto.

The detergents may be used to wash a surface of the dermis or body parts of birds that are exposed to or can be exposed to avian pathogenic *Escherichia coli*, without being limited thereto.

Yet another embodiment of the present invention provides a method for preventing or treating infectious diseases caused by avian pathogenic *Escherichia coli* using the bacteriophage ΦCJ25 or the composition including the bacteriophage ΦCJ25 as an active ingredient.

Specifically, the prevention method or treatment method of this embodiment includes administering a pharmaceutically effective amount of the bacteriophage ΦCJ25 or the composition including the bacteriophage ΦCJ25 as an active ingredient to birds that are exposed to or can be exposed to avian pathogenic *Escherichia coli*. Suitable total amounts of the bacteriophage ΦCJ25 or the composition including the same per day may be determined by a physician within proper medicinal judgment, as apparent to those skilled in the art.

A concrete pharmaceutically effective amount of the bacteriophage ΦCJ25 or the composition including the bacteriophage ΦCJ25 as an active ingredient to certain birds may be determined by taking into account the sorts and degree of reaction to achieve, age, body weight, general health condition, sex or diet of corresponding individuals, administration time and administration routes of bacteriophage ΦCJ25 or a composition including the same, and secretion rate of the composition, treatment period, and the like, and may differ depending upon various factors and similar factors well known in the field of medicine including components of medicines that are used simultaneously or at different times.

The bacteriophage ΦCJ25 or the composition including the bacteriophage ΦCJ25 as an active ingredient may be administered in the form of a pharmaceutical preparation to birds by intranasal spraying, or directly added to avian feeds or drinking water so as to be digested, and may be mixed in the form of additives for feeds or additives for drinking water with feeds or drinking water and then administered.

Routes and methods for administration of the bacteriophage ΦCJ25 or the composition including the bacteriophage ΦCJ25 as an active ingredient are not particularly limited, and the administration may be realized by any routes and methods so long as the administration allows the bacteriophage ΦCJ25 or the composition including the same to reach desired tissues. Namely, the bacteriophage ΦCJ25 or the composition including the bacteriophage ΦCJ25 as an active ingredient may be administered by various oral or parenteral routes, and examples of administration may include oral, rectal, topical, intravenous, intraperitoneal, intramuscular, intra-arterial, trans-dermal, intranasal, inhalation, and the like, without being limited thereto.

Hereinafter, the present invention will be described in more detail with reference to a preferred example. It should be understood that these examples are not to be construed in any way as limiting the present invention.

[Example 1]—Isolation of Bacteriophage that Infects Avian Pathogenic *Escherichia coli*

Example 1-1

Bacteriophage Screening and Single Bacteriophage Isolation 50 ml of a specimen obtained from chicken feces collected around Samwhawonjong farm in Gwangcheon, Hongsung-gun, Chungcheong Province was centrifuged at 4,000 rpm for 10 minutes, and the resulting supernatant was filtered through a 0.45 μm filter to prepare a specimen liquid, which in turn was used to perform a soft agar overlay method. The soft agar overlay method refers to a method of observing bacteriophage lysis using a host cell growing on top-agar (attached to a solid medium using 0.7% agar).

Specifically, 150 μl of a shaking culture solution ($OD_{600}$=2) of avian pathogenic *Escherichia coli* (E09-19) obtained from the Department of Veterinary Medicine of Konkuk University and 2 ml of 10×LB medium (10 g/l of tryptophan; 5 g/l of yeast extract; 10 g/l of NaCl) were mixed with 18 ml of the filtered specimen liquid, followed by culturing at 30° C. for 18 hours, and the resulting cultured solution was centrifuged at 4,000 rpm for 10 minutes, and the resulting supernatant was filtered through a 0.45 μm filter. Subsequently, a mixed solution consisting of 3 ml of 0.7% (w/v) agar and 150 μl of a shaking culture solution ($OD_{600}$=2) of avian pathogenic *Escherichia coli* (E09-19) was poured and solidified on an LB medium plate, to which 10 μl of the specimen liquid was added dropwise, followed by culturing at 30° C. for 18 hours, thereby identifying formation of plaques.

Since it is known that one sort of bacteriophage is present per plaque, the inventors tried to isolate single bacteriophages from the formed plaques. Specifically, 400 µl of SM solution (5.8 g/l of NaCl; 2 g/l of $MgSO_4 7H_2O$; 50 ml of 1M Tris-HCl (pH 7.5)) was added to the plaques and left at room temperature for 4 hours, thereby obtaining a bacteriophage solution.

Subsequently, 100 µl of the bacteriophage solution was mixed with 12 ml of 0.7% (w/v) agar and 500 µl of a shaking culture solution ($OD_{600}$=2) of avian pathogenic *Escherichia coli* (E09-19), which was used to perform a soft agar overlay method using an LB medium plate having a diameter of 150 mm wherein cultivation was performed until the bacteriophage was completely lysed. After completion of cultivation, 15 ml of SM solution was added to the LB medium plate and left at room temperature for 4 hours, thereby obtaining a bacteriophage solution.

To the obtained solution, 1% (v/v) chloroform was added and mixed for 10 minutes, followed by centrifugation at 4,000 rpm for 10 minutes, thereby obtaining a supernatant, which in turn was filtered through a 0.45 µm filter, thereby obtaining a final specimen.

Example 1-2

Large Scale Culture and Purification of Bacteriophage

Bacteriophage obtained in Example 1-1 was cultured at large scale using avian pathogenic *Escherichia coli* (E09-19), and then the bacteriophage was purified therefrom.

Specifically, avian pathogenic *Escherichia coli* (E09-19) was shaking cultured, and inoculated at $1.5 \times 10^{10}$ cfu, followed by centrifuging at 4,000 rpm for 10 minutes, and re-suspending in 4 ml of SM solution. To this, the bacteriophage was added at $1.5 \times 10^6$ pfu with multiplicity of infection (MOI) of 0.0001, and then left at room temperature for 20 minutes.

Next, 150 ml of LB medium was inoculated therewith, and cultured at 30° C. for 6 hours. After completion of cultivation, chloroform was added to a volume of 1% (v/v) of the final volume, followed by stirring for 20 minutes, to which DNase I and RNase A as restriction enzymes were added in a final concentration of 1 µg/ml, respectively, and left at 30° C. for 30 minutes. Subsequently, sodium chloride and polyethylene glycol were added to a final concentration of 1M and 10% (w/v), respectively, and left at 4° C. for 3 hours, followed by centrifuging at 4° C. and 12,000 rpm for 20 minutes, thereby obtaining a precipitate.

The obtained precipitate was suspended in 5 ml of SM solution and then left at room temperature for 20 minutes, 4 ml of chloroform was added thereto with stirring, followed by centrifugation at 4° C. with 4,000 rpm for 20 minutes, thereby obtaining a supernatant. The supernatant was filtered through a 0.45 µm filter, followed by ultracentrifugation (35,000 rpm, 1 hour, 4° C.) using a glycerol density gradient method (density: 40%, 5% glycerol), thereby purifying a bacteriophage.

The present inventors isolated a bacteriophage having a specific ability to kill avian pathogenic *Escherichia coli* from samples collected from chicken feces on farms, which was designated as "Bacteriophage ΦCJ25" and deposited at the Korean Culture Center of Microorganisms (KCCM) (361-221 Hongje 1-dong, Seodaemun-gu, Seoul, Korea) on Oct. 25, 2013 under accession number KCCM 11462P.

Example 2

Morphology Observation of ΦCJ25

The bacteriophage ΦCJ25 purified in Example 1 was diluted in 0.01% gelatin solution, and then fixed with a 2.5% glutaraldehyde solution. The resulting bacteriophage was added dropwise to a carbon-coated mica plate (ca. 2.5 mm×2.5 mm), acclimated for 10 minutes, and then washed with distilled water.

Subsequently, the carbon film was mounted on a copper grid, and stained with 4% uranyl acetate for 60 seconds, dried, and examined under a transmission electron microscope (JEM-1011, 80 kV, magnification of ×200,000) (FIG. 1).

FIG. 1 is a transmission electron microscope image of bacteriophage ΦCJ25, in which the bacteriophage ΦCJ25 had morphological characteristics of an icosahedral capsid having a size of about 83 nm with a contractile tail, indicating that the bacteriophage belongs to morphotype A1 *Myoviridae*.

Example 3

Total Genomic DNA Size Analysis of ΦCJ25

Genomic DNA was extracted from the bacteriophage ΦCJ25 purified in Example 1.

Specifically, to a cultured solution of the purified bacteriophage ΦCJ25, 20 mM ethylenediaminetetraacetic acid (EDTA), 50 µg/ml protease K and 0.5% (w/v) sodium dodecyl sulfate (SDS) were added and left at 50° C. for one hour, to which an equal amount of phenol (pH 8.0) was added with stirring, followed by centrifugation at room temperature and 12,000 rpm for 10 minutes, thereby obtaining a supernatant.

The supernatant was mixed with an equal amount of PC (phenol:chloroform=1:1), followed by centrifugation at room temperature and 12,000 rpm for 10 minutes, thereby obtaining a supernatant. The supernatant was mixed with an equal amount of chloroform, followed by centrifugation at room temperature and 12,000 rpm for 10 minutes, thereby obtaining a supernatant. The supernatant was mixed with 10% (v/v) of 3M sodium acetate based on the total volume, followed by the addition of 2 volumes of cold 95% ethanol, mixing, and standing at −20° C. for 1 hour.

Subsequently, the resulting substance was centrifuged at 0° C. and 12,000 rpm for 10 minutes, from which a supernatant was removed to obtain a precipitate, which was dissolved in 50 µl of TE buffered solution (Tris-EDTA, pH 8.0). The extracted DNA was diluted 10 fold, and then concentration of DNA was determined by measuring absorbance at $OD_{260}$.

Next, 1 µg of DNA was loaded on a 1% PFGE (pulsed field gel electrophoresis) agarose gel, and developed using BIORAD PFGE SYSTEM NO. 7 PROGRAM (size ranging from 25 kb to 100 kb; switch time ramp 0.4 seconds to 2.0 seconds, linear shape; forward voltage, 180 V; reverse voltage, 120 V) at room temperature for 20 hours (FIG. 2).

FIG. 2 is an electrophoresis gel photograph of genomic DNA of the bacteriophage ΦCJ25, and it could be seen that the genomic DNA size of the bacteriophage ΦCJ25 was about 39 kbp.

11

Example 4

Protein Pattern Analysis of ΦCJ25

15 μl of purified bacteriophage ΦCJ25 solution ($10^{11}$ pfu/ml titer) was mixed with 3 μl of 5×SDS sample solution, and then boiled for 5 minutes to perform 12% SDS-PAGE (FIG. 3).

FIG. 3 is an electrophoresis photograph of SDS-PAGE results performed on the bacteriophage ΦCJ25, and it could be seen that main proteins had a size of about 43 kDa, about 49.3 kDa, about 60.4 kDa and about 94.9 kDa.

Example 5

Analysis of Genetic Properties of ΦCJ25

In order to determine genetic properties of the bacteriophage ΦCJ25 purified in Example 1, DNA of the bacteriophage ΦCJ25 was analyzed using an FLX Titanium Sequencer (Roche) as a gene analyzer. Genes were recombined using GS and de novo assembler software (Roche) by Macrogen Inc. Open reading frame was identified using GeneMark.hmm, Glimmer v3.02 and FGENESB software. Open reading frame was annotated using BLASTP and InterProScan program.

Nucleotide sequence of the bacteriophage ΦCJ25 showed similarity to nucleotide sequence of previously reported bacteriophages (*Enterobacteria* phage EcoDS1), but it could be seen that there were no bacteriophages in which all fragments 100% coincide. Accordingly, it could be seen that the bacteriophage was a novel isolated bacteriophage.

The following Table 1 shows comparison results between nucleotide sequence of the bacteriophage ΦCJ25 and decoded nucleotide sequence of the prior reported bacteriophage in the art.

TABLE 1

| Query | | | | Subject | E-Value | Identities | |
|---|---|---|---|---|---|---|---|
| Name | Length | Start | End | Description | | Match/Total | Pct. (%) |
| SEQ ID NO: 1 | 39618 | 1 | 9030 | Enterobacteria phage EcoDS1, complete genome | 0 | 8653/9041 | 95 |

DNA of the prepared bacteriophage ΦCJ25 was analyzed using a DNA sequencer and the analyzed total nucleotide sequence is set forth in SEQ ID NO: 1.

Example 6 pH stability of ΦCJ25

In order to identify whether the bacteriophage ΦCJ25 can maintain stability at low pH like stomach conditions, stability of the bacteriophage ΦCJ25 was examined at various pH (pH 2.5, 3.0, 3.5, 4.0, 5.5, 6.5, 7.0, 8.0, 9.0, 10.0 and 11.0).

For the experiment, various pH solutions (sodium acetate buffer solutions (pH 4.0, pH 4.5, pH 5.0, pH 5.5), sodium citrate buffer solutions (pH 2.5, pH 3.0 and pH 3.5), sodium phosphate buffer solutions (pH 6.5 and pH 7.0), and Tris-HCl solutions (pH 8.0, pH 9.0, pH 10.0 and pH 11.0) were prepared at a concentration of 0.2M.

180 μl of each pH solution was mixed with 20 μl of a bacteriophage solution with $1.0×10^{10}$ PFU/ml titer to allow each pH solution to have a concentration of 1M, and then the resulting solution was left at room temperature for 2 hours. For a control group, 20 μl of a bacteriophage solution with $1.0×10^{10}$ PFU/ml titer was mixed with 180 μl of SM solution by the same method, and the resulting solution was left at room temperature for 2 hours. Thereafter, the solutions were serially diluted, and 10 μl of each of solutions in each dilution step was cultured by the soft agar overlay method at 30° C. for 18 hours to determine bacteriophage titer based on whether the bacteriophage was lysed (FIG. 4).

FIG. 4 shows experimental results of acid resistance of the bacteriophage ΦCJ25. In FIG. 4, it could be seen that the bacteriophage ΦCJ25 did not lose its activity and maintained stability from pH 3.5 to pH 11.0, as compared with the control group.

Example 7

Heat Stability of Bacteriophage ΦCJ25

If bacteriophages are formulated into additives for feeds among dosage forms of bacteriophages, heat can be generated during formulation procedures, and thus, the following experiment was performed in order to determine heat stability of bacteriophages.

Specifically, 100 μl of bacteriophage ΦCJ25 solution with $1.25×10^{10}$ PFU/ml was left at 37° C., 45° C., 53° C. and 60° C. for 10 minutes, 30 minutes, 60 minutes and 120 minutes, respectively. Thereafter, the resulting experimental culture solution was serially diluted, 10 μl of each of solutions in each dilution step was cultured by the soft agar overlay method at 30° C. for 18 hours to determine bacteriophage titer based on whether the bacteriophage was lysed (FIG. 5).

FIG. 5 shows experimental results of heat resistance of bacteriophage ΦCJ25. As shown in FIG. 5, it could be seen that bacteriophage ΦCJ25 did not show activity loss at 53° C. for up to 120 minutes, and showed activity decline of about 1 log or less at 60° C. for up to 120 minutes.

Example 8

Drying Stability of Bacteriophage ΦCJ25

If bacteriophages are formulated into additives for feeds among dosage forms of bacteriophages, bacteriophages can be dried during formulation procedures, and thus, the following experiment was performed in order to determine stability of bacteriophages against drying conditions.

Based on the results from heat resistance experiment, drying experiment was performed using a SpeedVac concentrator. 200 μl of bacteriophage ΦCJ25 solution with $1.2×10^{10}$ PFU/ml was dried at 60° C. under vacuum for 2 hours, and the resulting pellets were introduced to 200 μl of SM solution, followed by completely re-suspending at 4° C. for one day, thereby measuring titers (FIG. 6).

FIG. 6 shows experimental results of drying resistance of bacteriophage ΦCJ25. As shown in FIG. 6, it could be seen that after drying, as compared with initial titers and relative stability, bacteriophage ΦCJ25 showed activity loss of about 1 log or less when dried at 60° C. for 2 hours.

Example 9

Examination of Infection Range of Bacteriophage ΦCJ25 on a Wild-Type Isolated Strain, Avian Pathogenic *Escherichia coli*

Lytic activity of bacteriophage ΦCJ25 was tested for 46 strains of the wild-type avian pathogenic *Escherichia coli* isolated by College of Veterinary Medicine, Konkuk University (KU), 10 strains of avian pathogenic *Escherichia coli* isolated by Korea Animal and Plant Quarantine Agency (KAPQA), 7 strains of avian pathogenic *Escherichia coli* isolated by College of Veterinary Medicine, Chonbuk National University (CNU), and 26 strains of disease-diagnosed avian pathogenic *Escherichia coli* isolated by Komipharm farm (KF) in addition to avian pathogenic *Escherichia coli* (E09-19) used in the present experiment.

Specifically, 150 µl of a shaking culture solution of each strain ($OD_{600}$=2) was mixed, and 10 µl of bacteriophage ΦCJ25 solution with $10^9$ pfu/ml titer was dropped thereto and cultured by the soft agar overlay method at 30° C. for 18 hours, and then plaque formation was examined (Table 2).

The results are shown in Table 2.

TABLE 2

| No. | | Serotyping | ΦCJ25 |
|---|---|---|---|
| | KU strains | | |
| 1 | E09-1 | | 0 |
| 2 | E09-2 | | 0 |
| 3 | E09-3 | | 0 |
| 4 | E09-4 | | 0 |
| 5 | E09-5 | | 0 |
| 6 | E09-6 | O-78 | 0 |
| 7 | E09-7 | | 0 |
| 8 | E09-8 | O-78 | 0 |
| 9 | E09-9 | O-78 | 0 |
| 10 | E09-10 | | 0 |
| 11 | E09-11 | O-78 | 0 |
| 12 | E09-12 | O-125 | 0 |
| 13 | E09-13 | | 0 |
| 14 | E09-14 | | 0 |
| 15 | E09-15 | | 0 |
| 16 | E09-16 | | 0 |
| 17 | E09-17 | | 0 |
| 18 | E09-18 | | |
| 19 | E09-19 | | 0 |
| 20 | E09-20 | | 0 |
| 21 | E09-21 | | 0 |
| 22 | E09-22 | | 0 |
| 23 | E09-23 | | 0 |
| 24 | E09-24 | | 0 |
| 25 | E09-25 | | 0 |
| 26 | E09-26 | | 0 |
| 27 | E09-27 | | 0 |
| 28 | E09-28 | | 0 |
| 29 | E09-29 | | 0 |
| 30 | E09-30 | | 0 |
| 31 | E09-31 | | 0 |
| 32 | E09-32 | | 0 |
| 33 | E09-33 | | 0 |
| 34 | E09-34 | | 0 |
| 35 | E09-35(297) | O-78 | |
| 36 | E09-36(343) | | 0 |
| 37 | E09-37(343) | | 0 |
| 38 | E09-38(343) | | 0 |
| 39 | E09-39(353) | | 0 |
| 40 | E09-40(353) | | 0 |
| 41 | E09-41(376) | | 0 |
| 42 | E09-42(376) | | 0 |
| 43 | E102 | O-1 | 0 |
| 44 | E103 | O-78 | 0 |
| 45 | E104 | O-78 | 0 |
| 46 | E105 | O-78 | |
| 47 | E106 | | |
| | KAPQA strains | | |
| 48 | O6Q-035 | O-78 | 0 |
| 49 | O6D-044 | O-78 | |
| 50 | O6Q-140 | O-78 | 0 |
| 51 | O7D-001 | O-78 | 0 |
| 52 | O7D-022 | O-78 | 0 |
| 53 | 07Q-039 | O-78 | 0 |
| 54 | KWU-02 | O-78 | 0 |
| 55 | KWU-32 | O-78 | 0 |
| 56 | KWU-33 | O-78 | |
| 57 | KWU-43 | O-78 | 0 |
| | CNU Strains | | |
| 58 | A12-MRA-076-① | | 0 |
| 59 | A10-LSf-005 | | |
| 60 | A11-LSF-043 | | |
| 61 | A12-MRA-076-② | | |
| 62 | D12-JW-058 | | 0 |
| 63 | A12-LSF-083 | O-78 | |
| 64 | A12-MRA-076-③ | | 0 |
| | KF Strains | | |
| 65 | 12-001-3 | | 0 |
| 66 | 12-053 | | 0 |
| 67 | 12-055 | | 0 |
| 68 | 12-086-1 | O-78 | 0 |
| 69 | 12-086-2 | O-78 | 0 |
| 70 | 12-096-3 | | 0 |
| 71 | 12-175 | | 0 |
| 72 | 12-187 | O-78 | 0 |
| 73 | 12-211-5 | | 0 |
| 74 | 12-220-4 | | 0 |
| 75 | 12-220-6 | | 0 |
| 76 | 12-248 | | 0 |
| 77 | 12-261-1 | | 0 |
| 78 | 12-266 | | 0 |
| 79 | 12-274-1 | | 0 |
| 80 | 12-275-2 | O-78 | 0 |
| 81 | 12-286-2 | | 0 |
| 82 | 12-300 | O-78 | |
| 83 | 12-303-2 | O-78 | 0 |
| 84 | 12-304-3 | | 0 |
| 85 | 12-299-1 | O-78 | |
| 86 | 12-299-2 | O-78 | |
| 87 | 12-299-3 | O-78 | 0 |
| 88 | 12-324 | O-78 | |
| 89 | 12-338-1 | O-78 | |
| 90 | 12-338-4 | O-78 | |

As shown in table 2, the bacteriophage ΦCJ25 exhibits infection ability to avian pathogenic *Escherichia coli* (including O-1, O-78, O-125 serotypes), which is a major causative bacteria of avian colibacillosis in general poultry farms.

Meanwhile, it is known that O-78 serotype is generally the most dominant strain among avian pathogenic *Escherichia coli* isolated from poultry farms.

The invention claimed is:

1. A method for treating an infectious disease caused by avian pathogenic *Escherichia coli*, the method comprising: administering bacteriophage ΦCJ25 deposited as accession number KCCM11463P to birds.

2. The method for treating an infectious disease caused by avian pathogenic *Escherichia coli* according to claim 1, wherein the infectious disease is avian colibacillosis.

3. A method for treating an infectious disease caused by avian pathogenic *Escherichia coli*, the method comprising:

administering a composition comprising bacteriophage ΦCJ25 deposited as accession number KCCM11463P to birds.

\* \* \* \* \*

SEQUENCE LISTING

<160> NUMBER OF SEQ ID NOS: 1

<210> SEQ ID NO 1
<211> LENGTH: 39618
<212> TYPE: DNA
<213> ORGANISM: Artificial Sequence

```
<220> FEATURE:
<223> OTHER INFORMATION: Novel Bacteriophage CJ25

<400> SEQUENCE: 1
tcttcaatct taatcaggaa ccgtgagaac ttgtaggaca tcagataaga ccttccgatg     60
aacactgtac gtcctgacca atctccattg agtgtaacca cagttgagat ttcggtcaat    120
tcaccaaggt ccacgtaagc accctgactg tcaataagat agtagcgacc gggagacgga    180
gtgtttccac cataagcaga accaatgtca accgtagtct tataggtgtc agcgttgtat    240
gagtcaattg gtattatcat agacaccttg gagtcaacgt ggagtctata cggctctaat    300
ggaaagtcag ttgcctcctt gatgaactta aggtgctcaa ggtccacgcc gacttggtgc    360
tgacgaacaa tgaacatggt agagccaatc gacgcagacg ccagaatctt atcagcttta    420
gggaactccc agtgcgacca agaggcttga agctgtacgc cgtccttaaa caagaacttg    480
tagatgtaga ttcggttgta tgcacctgta gagttgacgc agatgtagtt ctcggtccct    540
gtaccttgaa tgtcaaacac cccgttaggg atataagaca gtacgtggcc agtggtatca    600
tcggcatcct tcacgtcaga cacatctgct acagcgaagt atcgcttaat gctggtgaat    660
gacccacgag gcgctgagaa gaagactgag cgtcctacag cgaacggtct ggcattatcg    720
cctacggcaa actctgagcc tacatcaagc tggatagact tcgaggtaag gacccctgag    780
cttgtcatca cgaactgcac ctcatctgac caaagtagta gctgctcact aaacggaacg    840
gcatacttaa ggattgagat tctagggtga cttacagcta cgtcaatagg atcgtcatca    900
ctcagtgtcg ccacactctt agggaagaac gcaaagtagc tggctgaacg gctcatgatt    960
acgttctcgc ctgacaagaa ccccagccta ttcctgtaga agaacacatc gttaatcgta   1020
gcatccacga agctaggcat agggtttgtg tcatcattac cagcaccacg cttagaccag   1080
tccagagtct tgaactcaaa ggagccgtca gattgtctca ccagagcatg tggcattgtg   1140
gtgttgtcga acccagtgac cactcccggc tctactgtct ccttccacgt cttagtgttg   1200
gagtcataca tcacgtaata ttcatcggcg ctactgttgg tctcaccttg aatcttaatg   1260
atgtacccat ttggagcagc aagaggcaac ttagagattg tctgcaccgt gtcgaggact   1320
gggctgatta gctggttagc gtagccatcc tccgtctcca ctgagttaat gtcagtccct   1380 gaagggcag tgattaacag gaatccaggc ccaaggtcga acgtgaaggt agggtaagca   1440
gcaacaagaa ggtctctcag agcttcaccg atgacctgag catccacctt atgagggtcc   1500
ttctcggcat cagtacctgc tggcaactta tgcctaacct taactcctcc gttgattcct   1560
accctaaggg cgcgaccata ctgtccgcca cgcaggttaa ttaaagcacg agctttacaa   1620
ttataaccag agtgtgcctt ctcgctcccc cctttaacga caaccttacg gttcacgatg   1680
aacgtatagt ctgcaacggt aacgacacgg atatcatctc gcgggttgga cgacttaacg   1740
tagtctacct caccggaaac tgagtactga ttaccactca agtcaactac ctgaatgttg   1800
gacccgttga acacgatgta atactgctcc tgctcatcac ggttaatcag gtggaactta   1860
gggttgctcc caacgtcgat gttaagacgt cgcttgaaga ctgtaggtgg acgcttctgg   1920
agtccatcac tttcggatga ccagcagtta acttgctcct cgccttggtc cgagaacctc   1980
aggatgtcgg gctgctggct aatgccacct ttaaggttct tgattgattg agtaattagt   2040
ggcataggcc ctccttaaat catactcatt aggacgtatc cctcagcgat gtcaccaacg   2100
tcagcaatgt ggacaacctt acgtgctacc tgttgtccag tatacccgtt gtcccactca   2160
ttcaggataa gccagtcgcc aaccttaaag tcccggtcgt taagtctaag ctctgctgtc   2220
```

```
tttagaccta gctgtaccgg accaaagtgc tggcggtgaa tcttcaggtt gtgactagcc   2280
attagtccct cccgatgtcg gacatcatgt tgtagcgacc agtgtccatc tcgtattcca   2340
tgacctgctg atagagctct gcttcctgct cacgaaggta cagttcagac tctgggctac   2400
cgaagaactt agcgttgaac tcacggctag ctttagtgac gatgtagtcc ctgaagacca   2460
caggcatctc ggagaatggc ttcatctcca caagctctac cgtgataggg tcggtgaaag   2520
tggttgactg agtggacagg tcgtacaggt atccacccat gttgctgtag tagctggtgg   2580
ccccagtggt cattacacga aggtatgacg gcaagaatcg aatcctattg tcttggacat   2640
caggtgtcag gacagcagct tcgttgatgt taaagttcca gcctttagct tggacctgac   2700
gattgacacg atgcagtata cgttgagcgt tcgagacgtc agcgttcccc tcgtcaagct   2760
gtaggactgc tggttcaccg atagcagcta acatatcgtt gatggcgtct aagtcatcgt   2820
tagtattcag tggaatgtat tgagccataa gtctcctctc gctttaagca aaaaaaccc    2880 ctcaagcacc cgaaggcacc caaggggttt caattagttg ttggactcag ccagtttagc   2940
ggccctgttc gcagcacgag tacgcgcagc tttctgttga ggagttaggg tctcctcttc   3000
aggtgcagcc gctactgtag cgacgttagg ttggctaaag gtgcttacgc cgctgcgctg   3060
aaaaccagtg cgccagccgc ttcagggcgc agaccaccgt gacccatagc gtacttacca   3120
acaatcaggt cgccctgagc atcgacgtca cggtcacgtt ccagcgccaa gtcacgcagc   3180
ttaacggtac ccacagcaga acggtgagag aacagaccca caacgttgtc catagcaact   3240
ttaacgtcgc cagtagcagt tgccgggaat gcgtgtttct gaccggaagt gatagagata   3300
ccatcgtcac cacgggtctc accagcgcca ccctgtacaa gatgcggaac ttcaacaaca   3360
acgaagccca tcacgttacg gatgttacca gtctctgggt caatcagcgc agcatagtta   3420
gcagcgttag gcatcagagc ggcgaggatt gcagagtagt tgtccggcgt ggtgtagaag   3480
taacggtcgc cagcaggaac gtagttggag gtcagcttcg cacgagcaat ggtcagttga   3540
ccaatgattg cttcacccag tttagccggg gtgtcgaggt cagctttctt accaacttcc   3600
agtacggacg cagtacccag accagcgatg ttctcgttgg atgcagctgg gaggttacac   3660
aggatagcca tttcagccag aacagcacca tcggcagcga tagccagagc ctcacccaac   3720
tggttggaat actcgccagc cacgtcatag tggttcatag cgtcttcaat gtcgaaaatc   3780
atcacatcgg cagtcagcag accatcaatg gtaatcactt tctcggtatg tttgatacct   3840
ttacgcttat ctgacagtcg ctcacctgga gccagataca caccagaggt gcggcccatg   3900
accgggaact gagcagactt accgttctga atggtacgga caatatgctt gtcagccgtt   3960
acagagcggc gagtgaatgc ggtcaggact tcaccagcaa agaccttcag gaacaacgcc   4020
agagcgtcgg aactggatgt accttttacct tggtctgtac caattttctg acccgtaacc   4080
tttgccatat gataattctc ctattcaatt gaaagataaa gtttattact tactgtatgc   4140
ccaatccgta tggactgaag taatagggaa accttgagtc tgtctcttgg tctccctata   4200
gtgatagttt agtcctacag gcttgaggcg gctaccttag cgcgaacttc catcgtgtac   4260
ttagcgtcac gcaggtatcg cgggtcactc atagccttaa tcatgtcagc cttggagctg   4320
aatgcttcgg tctgaggagc cttaggtgcg accacaggtt tagcctgagt ggtgatggta   4380
cgctgaggtt taacacctac agctttaccc agagtcttgc cagccagatt cagaagagct   4440
ttggtagtag caatgtcctt acgaacgata gcagcttcca gtgcttcacg agttgatggg   4500
tcgttggatt caaggtgtga caggattcga ttaaaatgtt cagcaccacc agcgtatcga   4560
accacaccag cagcgtactg ttcagccaga gcttcctgac cacgtacaaa cgaatctacg   4620
```

```
aaacgcttgg tgtaacctgc ttcctgcaac ttagcgtagg atgcgtcaga cagcttaccg   4680
tccttggcgt attcagcctt gatagcggta atctcatcag cagtgacctt gccagcttct   4740
acagcagaag acaccatgtc gtcgaatgca gcttcgtttt catccagagc ggtgacactt   4800
tcggtcagct ctttaggtgc atcaccaagt tcgacgaact caggttgctc accatcgttc   4860
tcagactctt cgtcatctga ctcgtggtct tcttcacctt cagtctcttc gacgttctcg   4920
tcttcttcgg tcgcctcttc gttttcgact tccagttgct tgaaggtaat agcgtcgtcg   4980
ccatcacgaa cagctacgtc ctgttcaagc atagacttct ggtattcgtt caggtcctca   5040
acggaaccag tgattgcatt agagctaacg ccaaactcgg cataaactga ttgagacatt   5100
gagtcattct cctttaagtc gttaataggt aaacacctac ttgcagtgtg gactaacgg    5160 ctaccatatg gtcgacttag tagctcttac tttcggtgtt cctatagtga tagtttaggc   5220
ttgagccatg tcctcaccag ctccctgacc tacagcagca cccatgttag caccagcagc   5280
agacgcaccg ttgaccacag ctccttgagc ggattgttca gcaatacgtt gcatcttctc   5340
gtcctgagtc agaagcagac cagcggtgtc aattcctaag gcattcagta gtcgcagctt   5400
cagggtcggc aagttaatgt ccgggtcctg ttgcagaggc tgtagcccgg tcatcatgtt   5460
aaccgcctga gtcagcttct ccaagtcctg accacgacct aacgcttcca gaccagtgga   5520
gaccgtaggc tctaccgctt ctttcggaag gtcaggaatc atgccagcag actgaagttg   5580
gttcatcagc acacggacga taggtaactg aagctcttgt gactgtaccg agtacacgcc   5640
ccctaaggtc gcctccagtt cgccagcaac ataacgaatc tcttcagcag tcactcgctc   5700
agcattacgc tgaacagcac tattaagaag gaaggcccag cctaaacgtt gctcgatagc   5760
gtcagccacc gacttggcaa tcgtaaagtc ctgacctttc gtcagttgca ggaagttgat   5820
gtcctcgacg cgaccagcca cgaactcacc tgtagccgcc ttgttcagac gacgaggttg   5880
cgtgataccg ttcgggttaa cgaggcccac caccttggag gctaccttag ccattttggt   5940
gatagcttct gtaatcgtct ccagcgagtt caggtctcca agatactcct cgcagtaaga   6000
acgaccatag tcttcaccat ccagtcgaac cattcgtacc gggatgtatg gacatgcagt   6060
cagtgggtag gaaccctcgg tccctgctac ctcaatgcct tccacttctt catagcgcaa   6120
atactcgtcg tcctgacggt agatgtgagt atatacttcc agctctgtgt caggctcata   6180
gtcgtctgcg ttgagttgtg acttcacgtc ttccggtaga gcactaaacg ctaccttgtc   6240
gagagtcaca atctgcaaga tattaccgaa agcatcacgt tgaacaacgt aggacactaa   6300
gcggtacatt cgcataggac tgtaagtacc ttgttcaggc tctggaatgt agagcagaca   6360
gttaccggag acgataagct gcttcagagc ttcgaacaat gggacacgga aactgttagt   6420
ctccatgtag gccatcaaca cacgctcgac catagccagc ccttcgtcaa cacgagccgc   6480
agcctctgag tcctgactca aggtcttggc ctcatattcg gagactgtaa gtcgcatcca   6540
cggtgactga gggaataatg ccaacatcag ctttgcagcc aagttgttca agcagcgagc   6600
acctacagct tgccacggag ttgtgtactc agtagacgag ttgtcggact ccttaggaaa   6660
tagtgacggg atagtgacag cagcacagtt ctgagcgcgt gtctcatatg gctgtctacc   6720
gttctttagt ctgtcataga ccgctttagc tccttcagca gcgaacccct cacgttcagc   6780
cattcgtcac ctccttaaat agaaataccg ccaccagagg tgcgagagac ctgaaggcta   6840
cgcttaccgg aacgcttcac tttcttctcg tcagatgtgg ttgtttcagt atccacatcc   6900
tccactttgg cgttcggtac ttccactggt gctgctgggg cctgagcctc aacaaccttca  6960
```

```
ggtgcatctt cagctccaag accaacggtc cctagcgtac ttttcaccac tttcttgaaa    7020
gccttactga ttgatttacc cacggttaat ctccttagtt gttacgatgt ctaccgaccc    7080
agaaacatgc ttgacacgag aataccagcc aagaccccaa cgcttgcact cttcgtttac    7140
gatgtgcctg acagtctcaa gaaccttgcg ggaggactgc gagtcacgac gaatagcgac    7200
gattgaaagg tcaagaccgg gagtcggtcg gtgccaagat gcggtagcta gcatgtagag    7260
atacgctact ggttgacctg agacatcgta gattgtgtac tcttcaccat cgaactcgtc    7320
agcaatacgg taagtatgag ccttgaagtc ctcgaatgac ttgaagttag actgcccgtc    7380
ttcccagagg cgacaagcgc acatgtggcg accttcgcgt gagttgagat atggtagcat    7440
tgtcttaccc catgttgacg ccagaggctc gcatagcgcg acttactgac gatttatctt    7500
taggtgcaga ctccttcttg accttcaggt ctttgatacc tttggtctcg ttggtgtcca    7560
catccgattc agcccgatg tcaactgacg caacttcctc actcagaggt gctggttcag    7620
gtgcttggac cgaaggcttc ggagtgctaa tctttggact gaaacacata gtccctccta    7680
cagttaatca aactgaacgg tatctttcag ctcacgacgc atagcaatcg cagagtcgag    7740
agtgtcagag caatactgga gacccttgat aaaccctgca atgaacgcat cgctgtagcc    7800
ctgctgcttt aggagactga tagctcccat cttctcagcg tagcttgcgt tgaacagtac    7860
gtgcagaaac tggatggcag actgggagat gttcgggaca tcaagtcttt cttcctgtaa    7920
ctgcttaaca acgttttcaa tagcattaat tgccatcttg aatctcctct ttaagttaag    7980
actaaagtct atcttatagt catatcctag gtcctaaagt ccctatagtg atagtttagt    8040
gtttcaccta tggatgactg ttggattgat aggatatgac tatcggttag actcagtgtt    8100
tagggcggtt gttcgacccg aaccacttgt acatgcagta aagggccaga agtccggccc    8160
agtagattac atgatggtg tccacaggat gacctccttg gacttagggt catagtcgga    8220
ggctcgacaa atacgagcga cctgagcttg gaccagaagc tcctcctcgg tcatcccagc    8280
tttagcagcc agtgtaacca tgcagtccca cagcgtcatg tcttcacgct tcggatactt    8340
cttccactca gtcttaatct ggcctttgtt cttaccagtc ttaagctcac ggctctcctg    8400
cacgaagtag tacggctcgt caaggaacgc acgagtggtg tcctcaccca ttcccggaat    8460
gccaccgtag ccatctgtag tatcacccct tgatggtctgc tccatgtgcc agtagtctgc    8520
ctcggcagtc gtatgactca ggatttcacc agtggttaac cagaagaact cacagttcgg    8580
gatggtcttg aagtccttat cgcaggacac cagcaccgca tggtcacatc caacaatctg    8640
aggtcgggtc ccgatgatac ccatacagtc atcccctca agcgtaggac gcaggaagct    8700
gttgaaccgt gggtcagcca tcacttctgc tacgaacttc ttgtaaccta caggcttgcg    8760
agaaccttta cgattggact tataggtagg cagaacctcc ttacgccagt tgttatcgtc    8820
agtaaagcac atcacaatct tagcgtcttt ccacgccttg cgcttcttga cgatttcaga    8880
gatggtgttc tcaaggatac gacgagcctt ctcatggtcg cagataatgg tccagatgtc    8940
atcacccag tctgtctcgt cctcggcagc agccatagaa gagaagacca gatagtcacc    9000
atccagaacc agagctatct tcttctcaga acccatcgtc cagacctcca gtagccatag    9060
cgaccatagc tggcatcaaa gaaactttcg gctccttaat acgttcgaga gtcacctcag    9120
gctgaagcca tttgttggcg aactcgtggg ccatgtcgtt gtcctctgag tttaggtggg    9180
acatcaggtt ccagaagttt gaagacatct cagtctcatt ctcaaccggg cgatatactc    9240
cccagtcatt tacctctgaa ccatagctgt cactccacat accactggct acgatggtca    9300
gcccgatgaa cgggcgccac tcataggcct cagcgggaga ctctgtatat gactcaacgt    9360
```

```
ccttctcggt caaggtgtat gaccaagatg cgtagaactc agcgtacttg cggtgctcct   9420
tctcgcactc acccatttca aggaccagct ctttaagact ttcaggtatc ttcatagaca   9480
gcctccatgt tggttcagga acttaacgcc ttcagcggta atctcccacg caccattgtt   9540
acgcccatcc gtagacaggc agctcagatg tccacgactc gcagcctcag ccacaagtgc   9600
agcgttgttg cgcacatagt tggactggaa ggtcttcggg caggacttaa gggccgctag   9660
gacccgtaag tattcactca ttgcttgacc tcgaatcgca ggttggacac accgaactgg   9720
ccagcaccaa aggcgtctac cagctctttc ttgatgttct tcttggcgac aatttcaagg   9780
gcagactcag ggcctaactc gattgctgct ttgaccagag ccaactgaaa cccatccagc   9840
ttcttaccct cagcgtaggc tttagtcgtc tcagccagtt ggcgacacac ggtctcttct   9900
tcctttgagt tgataaccat cttcaggtcg aaacttacac gaatacgttt agtaatagcc   9960
attggtaaca ctcctttccg ttaatgacat tctttccacg tgggtccaat cttaccctca  10020
gtatcaagaa cacatttaaa gttatagaac tcacccacct tacgcatagc aagctgagca  10080
atcttgacga cttcttcggc aatctcctga gtacgacaag ctacttgaat ctcatccttt  10140
ctgtattctc ctattgctag gagtgtcgga ctatatcatc agcctttgag ttgactgtct  10200
ggcgcttcgg gtaacgaggg aatctcaccc tcggccctac tcctttcgga tagtctctac  10260
gccttccact ctctaatcca cttacacgcg gcagagaacg taacaccaaa cttctcacct  10320
aagtgtgttc ctgtacatcc agtctccagc cagtattcct tcgctgactc tttatggtca  10380
gcgtagcgtt ccctgttttgt cttgactgta tgctcagacc cttctagtaa ctggagatgc  10440
tctgcgttac agcatgccct gttcctacac ttgtggtcta cttcataccc ttctggtata  10500
tctccgtgct gttccttcca gactgtcctg tgatacatct ctaggacacc gttagtcctc  10560
tttcggaaat aaccatcagc attaagtttg tgtgacgtag ggatgataca accactctct  10620
gtggtcgcaa ggattaactt cttgcctctc atatatcctc cctatggctt ggctcggtat  10680
tgccctagaa gggtttcacc gagttcacca gatttaatgt gcacaatgag atagtttatg  10740
cacccatgcc atatatgcaa agtctccttc ccagccgtga acataccggg cctcttctag  10800
catacgttca gtctcgacaa tccagtgctt acagactacc gcaccatcgc cttgaagtag  10860
ggcgttaagt gctgagtgtg gagaccggat gtgaatgcgg cgaccatcaa gtccacgcaa  10920
ccaacggcgt ttccacttga cgatgttctc accatctacc cacttagagt ctgagattaa  10980
cgtattactc acagcttccc tgaggtcctt gatggctggt gtgccctcaa tgaatttctt  11040
catgagagct gaaccttcct tcttaccacc gccgactatc agtccaatct tcgctgcgcc  11100
tgcaccatac aggaacgcat agatgaacgt cttggcgttg ttgcggaaag cctcatggtc  11160
gtggctcgac ttatcgcgtg ggacgttagg tgctaaccca gcgtttactg cgttggccca  11220
gtggatgtca ccttcgacca cagtcttcgc ataggcacca ccatcaaacg gagccgctcg  11280
gttccccaga caacgaagct caagacctga ggcatcaaca cccacttgaa tccaagggtc  11340
tggcttaccg tccttcttat tccacgctgc accgaaggca ccacggcaag tctcaccata  11400
cggagcaccg ttagcaggga cctgagccat gtttggtgaa ctatgggtcg cacgtccggt  11460
tactgccccg catgggttga ttgaaccgtg catacgtccg tctggaccta caagtttcaa  11520
ccatgcgttc ttaccttcag ccacctgacc tatgcgcttc tggactacaa gatactcacg  11580
gaccagctct acgcaagcct gagcctctgc gtctggtaac ttaacgtgtt ctaacgtctc  11640
gtcatcaact acaggtttcc cggtgtcagt gaagtccaca ggttcccatc cacgctccat  11700
```

```
caagactttc gctaagtggt ctccgctccc cggattaaac tcaacgtaag tgataggtgt   11760
gaatggtgct ccctccatcg tgtctcgtga gtcgaactcg caaggctcca gtcctaggcg   11820
ttgagctttg ttcttcggct tcttgaatac tgacccgacc ttaggataca cgactcgagg   11880
atacttcgga aggtccttgc ctgtacgtgg gtgcttgaag aactccttgc ctcccttcgg   11940
tgcataccag ctaccgaaag tcgaacgcag cttgtccagt agctctgcac gtttgacagt   12000
gagttcacga tataagcctt cgaccatctc ggtgttcatc ggatagccgt tacgttccat   12060
cttcgcacag gtccacgcag catcatgttc cagacgcaac gcataaatct ggtcgaaagc   12120
gaactgttca gactggaagt aatacttgtc agtcagaaac ttcttgaaca acgccagcgt   12180
gaccacaacg tcttgaacgt tatagtccag catctcctga cacgggaaca accattcgtc   12240
cccagcctta tattcgatac cttcagcctt gcacttggca acgtaatcgt gtttgtactc   12300
acctttcatc tcaccgagac gatagcccca agcctcaaga gactgacgtc ccatcatctg   12360
aggtggcaga cgacctgctt tcaccgcgcc catgtctgag aacttaatgt ttggatacat   12420
caagcgagct agcaccaagg tatcaacaat tcgaccctta ttcacattta ggttcttacc   12480
gaagtatttc ttcttcagta ttttcaaggc tggtatatca tagttcacac cattgtgcag   12540
aaccagcata ccgtcagtgg atgccataat agattctatg cggtctatat attctttgaa   12600
cccacctgtc agcccagtca taggggcaac accatatttc tcagtagctt gagttccagc   12660
gttaatgata caccacagt ggaactgtga cacagtgtct agtagaccgt cagtctctat    12720
atctgtacca tagaatgagt tgagattaaa catcatattt ctccaagtac gttatagcag   12780
ccctaagcac ggctaccttg tcaccgaact taccaagtgc gctattacat gtgccacata   12840
gcaatcccct aacactacct gagtcgtggc aatggtcaac gtgggctata ttattcttac   12900
tctcaataga cccatgcttg aagataatgt ctgagcatat agcgcatctg ccattttgac   12960
tatcgaacat agtgtcatat tcctcaagtg tgagaccata ggctttctta agccaagact   13020
tacgggcaga tagacgatgc acctcaccgg cctctgtacc tttgtttcgg tgatatcgcg   13080
acctattatc ctcacgaaca caggatatac accacccatt tatcttcctg aactcagtgg   13140
actcctttgt ggagccacat ctactgcaag tcctcatatt gcttctcctt tagttataag   13200
tctaatcata aaggccactc gatgtgaatg gccttgagtc tagacctaga agtctgtacg   13260
caagaagtga tacataaact tccggttagc tttcttccat gccttagagt cgaacctttg   13320
gtctcccaga atgttggaca ggcaggtcgc ttcgtcactc caccatttgt acatgaaccg   13380
atggtagcga gctttaagtt ttcttagcaa tgtactcctc cttagaagtc ttggtcttcc   13440
cacgagccgc tatcctcttc tccgctgcta ccagtgtagc taatcggttc gagccacccg   13500
gtcgtcttgt tgtattcgag gtgtcctgcc actccagtgt cacccgtaaa acgacactta   13560
agcagacgaa gttgaacaat attaggagta tcaccttgct ggtttcgctc aagggcgatg   13620
atagtatcag acagttggcg gagagcacca gaaccacgta ggtcagtgat tgaaacaggt   13680
cgtccttctt catgcgattt acctttctct gggttcttca ggtgacatat gaccacgaca   13740
accacaccct tcgtcttcgc aaacttcttg agacgagtca tgatacggtc aatggtctta   13800
cgttcatctg agttatcttc catgcccgac acaacgattg agatgtggtc aagcagtatg   13860
acgtcacagt cgagaccgtc caccatgtag gccaacttag cgaacaaggt gtcttcctct   13920
gactcggcga atgaatcgta caggtggaac ttatcgtctc cgaacagctt gtcataccat   13980
tcgtcgaacc gtccatcctc taagatggct tgcttcagtt ccttgctctg gcgtagacgg   14040
acgttattgt ccagacccat aaggtcctga actgtttcct ctactgcctc ctccagcata   14100
```

```
gccatacccta cacgcttgcc tcctctgccc cactctaagα ggagctgacg gacgaaggta   14160
gacttaccca tgcctgaccc tgaagtcacc atgataagct caccagctcg cgcaccaagg   14220
gtcatcgcgt tgagtgttgt gcaggacgag aacatgagac cttcagtctc tgccttaagc   14280
atagcctccc gtgtgcggtc cttaagactt gctgctgata ccacaccagc cgggacgaaa   14340
ggtttagcgt tccagatagc atcggtgatg gccttgaagt ccttggcctg aagtgcagcg   14400
ttggcgtctt tgtacccgtt gatgaacgcg accttacccc gacctgctgg taagactgga   14460
gctgcatcct caatggcctg acgacccggt tcatccatgt cgaacatcaa gattatctct   14520
tcgaactggt cgagatactc aaggttcgca gccatagctt tcttcgcaga cttagcgcct   14580
aacggaagcg agaccacagg atactttccg tcctgcacct gagctacaga cagagcgtct   14640 atctcacccct cagttatgac tatcttcttg ccaccgttcc agagctgaga gccgaacagc   14700
atgtcagact tgacgctacc gatagcagtg aagttcttct cagcgtctcg gactttctgc   14760
cctaccttgg tcccggacct gtcgtaataa tcagcgacct gaaccatctt cccacccatg   14820
ttacctaccc agtagctgta cttcttacat atctccatgc tcagactacg ggctggtagt   14880
gggacatatc gtccagcgtt ctcaccgaac gttaacagat tgctcacttg cttctacct   14940 cctgagggtg tgtatccctc ggtcaactcc atgtctcctt tcttccatgc gactgaaggg   15000
tcacaggcga agcagtacat gtgtccatct gagtaaacac cattggcatc cgaggaccca   15060
cagtctggac actgggtgtg atacagaaag acactctcgt cgtctcggtc atcgtatgac   15120
attggtcact ccttaatcac aagtgcgaac agagggacag gactctcggt cccatcccta   15180
aggtgatagt ttaggctttg aagaactgag acaactggtc agctttggtg tcagcctgac   15240
gtgccttcat gccagcttcc agtgacgcta ttgtcagctt gtcagccaga gcagaagcat   15300
cagccgcgcc gtcagcagtc ttctttgcta cttttcgttc cagaaccgca gcacgacgat   15360
agccacgcac caccagacga ccaagaaatt ctataagttt aatcattggg ttgttctcct   15420
ttagagttta ttaaccgcgg tctgaagtga ccagttcgtt ggtagacatc cagcgttgta   15480
agtcgaaact tggcacgcc tttggcgcta cgtcatggtg agctttgatt tctgcctgag   15540
gatacaggac cttcaggtca tccagcttgt tgcgcaggga gttcatctgg gctggcgtga   15600
agttagcttc aaactgaccc ttagcgttga ttccacctac aaggcagacg cctactgacc   15660
gggagttcca gtccttaaca tgtgacccta cgacattgac cgggcgaccc tcttccacag   15720
tgccatcacg cttgatgata aagtggtagc ctacatccag ccagccttgc tgcttgtgcc   15780
acatacggat ggtctctacc ccgatgtcca tatctggctt ggtagccgaa cagtgaacga   15840
agatagcgtc agtccgggac cgtgggttga actgaacctt actcaccatc gtacaccacc   15900
agctctacag ctacgaggtt aagatgactt tggaagcggt tagcatccgt ggtgtgcatc   15960
tggagcaatt tatggttgaa gacgtgagag ttactaatct tcacgtacac ttcacccggc   16020
ttaccgtgga tgataaacga atagcctacc gggattttat caatggtcag acgcttacga   16080
acgaccttaa cttcttgagt catcacttaa ctcctttctt cttggggatg aggatacctg   16140
aaggcagacg tacagtcgcc tcccgaagcc actcaaccgg gatgaactta tcggcaaact   16200
taaagccgtt cttttcgcac catgcgccat acgtggtcgg agacccttttg tataacttgg   16260 agcgggaact tgagaacacg aaccggatgt ctaactctgg gtgctgttct cgtaccagaa   16320
ggtgcttctt acggtcatca ctatcgaaga taccttggt ctccacgatg ataccgtttg   16380
gaaggataaa gtctggtgtg tacttgtggt cggaagccgg aatcacatag ttgatataat   16440
```

```
ggctttcgta ctccgctttg acgccgttct gttccagcca ctgctggttc ttggcttcaa   16500
gtccagagcg gtaggcaccc acagagtgcc cccgttttgc agaccattgg gccattagaa   16560
gtcgtaatca ccaccagagc cagagtcgtc accaccttcg gaaccatcgt caccgaagtc   16620
gtcagacccg aagtcaccgt cagtcgacgc tttgtagcca ccagagccga tgtcttcatc   16680
gtcactccag ccaccatcgc caccactgcc ctcgccggac cactctttca gttcgaccag   16740
aaggcaggac tcaagctgga gcttaacgct tgcaccagtc gcagcgttcc acttgaacgg   16800
tagtacttta aactttacct tcagctttga gccagcgcca atattcggga cgtcacggat   16860
taacttagca tcggtgtcgt agaaccgtaa tacgataggc tctgacttac catccttcag   16920
gtaagacgca aagcatttga acttcatggt aacagtgcca tcaccgttct caatccacgg   16980
catgtcgcct tcacgcggtt caataggctt cttgccacgc tgaacctgag gtgggttctt   17040
ctcgtggtct gcgagtgctt tgcatgcgc atcgtcgtga atcttctgta agacatcaat    17100
catcttacgg accttcgggt tgctcaggtc gaatgtcagg ttgactttgt gttcaccacg   17160
ctcgttgtac ttggtgtctg ctttgttcag ccatgcgtaa ggctcaacga tgccagctac   17220
cggagtggtg aaagtcttca gttgctcttt agccattggt gtaaatctcc taattaaaag   17280
ttacgaactg gacgtctgtc ctacagtgat agtttaggtc tcaggacgaa tccgtccgac   17340
cacaaaccca gcgtcctcat actcttgtga cttcagggta gcctcttcaa gagactttgc   17400
gtacaccgga acctcgaagg attgaatgcg gccctcaagc tccacgatgt atttcttctc   17460
aacctcagtc ataaaccgcg ctccttccat tggttgtata acgtaatgta gtccgggttg   17520
agagtcttct cgtacatctc ccggcaccac tcactcggca gcatagcact tacctttatg   17580
caggtcgaac agctcctgat agaaggctgc tttgttcagg tccttctcca tagtcgccag   17640
ctctgacttc ttaccagctc ggagtcgata cttcaggacg ttacccaagc agaatccacg   17700
gaactcgctc acagtcatgg accgggcgat aatctcaatg gactctacgc cgtcaaagac   17760
ctgatagtgg gacggcttgc gaacgccatc aatttcttgg agtttgttac ctacaagttt   17820
accaacgtga gggaagcggt cgtcaccatt acacgcttca cagtatgtgg tgctatcaca   17880
gtatgtcatc agagcgcctc cttaattacc agaagtgcca gcttaatgcg aggccatttt   17940
gtaacgacca caggcacatc aacttgttct ttatccatag ccttcagcat agacttgcgg   18000
gtgactagcg catgaactgc tggagacaga gccactgtct taccaaagcg gggtaatggt   18060
tgattagctt tatggaagct gaatgggcta tgcgacaggt ggaagcttcg agtaaatcgg   18120
ttgaacatta agttttttaga cataaggttt ctcctttggt cggttatggt tgtcctatag   18180
tgatagctta gggtcaggct ggggccaaga cgatagcttg ctagcacaaa gcaaagaaac   18240
ccagcagtcc gaagaccact gggttgacgt tataaggaat ctcttaaggc taccgcctcg   18300
gctatggtat cgaacgtacc gtatgactta ctctttatcc gcagttgcca gcgaccagtt   18360
gatttctgat attgaacgta tttctctcca gattggcagt gactacgggt tggaacgtta   18420
gttaggttca ccgcctgagt cacacacctg aggttctcaa tcctgttatc tgaagggtcc   18480
ctgttgatat ggtcaatcac catcccttct ggtataggac cgtgggttag ttcccagact   18540
actcggtggg ccagcagttg gccctttgtc gtacttagaa tccagtaccc atcctttcgt   18600
ctataaccaa gatgtctacc gttaggttg gagactccag agggagccgc cctgtctgct    18660
ttaaatcttg accgtagggt cgtcctcagt tccacgccac tggtcgaacg agggatgccg   18720
tagtaagcca cttggtgtct cctccatgta ggtaatctgg caggcccagc ctttataata   18780
atcagggtcg gacttaacgt tttcggtgaa ctcggacatt agggcgcgac taatgttagt   18840
```

```
tgcggagacc tccatcccgt tctcaagcat aacgtcaaag ccgatgacca taccttcgtt    18900
ggctagacct tctgttcccc ataggccg tacaacgtga ccgtctgcct cttcgcttgg     18960
tttcatcttg aacatacctg acttcttgcc acgcttccag cgtcccagtg gatctttaac   19020
caccagaccc tcatggccct cttctctctt cttctcatac aagtcagtaa gctcgtctaa   19080
gctaaacact gtatgactct cagatagcac ccagtcgatt ccgggaagt atttctggag    19140 gagagggacg acagcttcgg ccttcaggcg tgtgacgcta tggataggac cttcggcttt   19200
cgggttagca atggttgtca tgttgatgac accgtagacc acaaccttaa gtcgtgaccg   19260
ggctacccag aacgggacct tcttgccacg gcccggatag cattcagcga actcctcgtt   19320
gttaggcttc agccacttcg ttcggatgag acctgaggat gtgttgaagt ccacaccttt   19380
gaccatgacc tcgccatcaa tcatcaggcc aacaccttcg tagccagctt gacgcaggaa   19440
ccatcgccag tcagcttggg tccacgcgtt acctaactca gagttcatcc actccaaggc   19500
tggcagaggt ttagactcac ggctcagcca gtaggtctca ccttcacgca ggaccaggag   19560
attcaggcgc acaccatcgt acttcacctc agcttccaga gacccggctg cttccagtgc   19620
cttcttaatt ctagactcag agtagtctac agcgcggtgc gggttagttt taatagtcgt   19680
agtcattata ttttctccat gtgtcgagtt ggttagcgag accgttaagg aagcctgttg   19740
cagtgttata cagtgcgtct tcagagtaat gtccgaaggt cttaagcgcg aagatgttac   19800
ccgctctatc ctcgacttga agtctcatgc actccatcct aagaggcgcg tcgtaccagt   19860
catgctgtat cacgcagaag tctaactgat agagcctgtt acacgctgct ctgaaagcgt   19920
tgaggttgcc aatataaagt cggtccatag cgttacactc ctacgaaata cttctcctgg   19980
ttgaccagag agtctttacc ttcagcatta cggaaagcac ccttgacacc ccctccacgc   20040
ttggtcttat tcagcttgcg tcccttcgga atgtaacctt cagtctgctg acgttcacgg   20100
atgcgctcga agttgatagt attctgatac atacggttaa atctccagta gtgtttattt   20160
agggttaatc atgaaggcca cgactttgag tcatgacctt gagtctaatc ctatagtgat   20220
agtttaggtt aacctcttct gcgttggatt aaggtgaata ctgcgagtgc tccaagccac   20280
aaggccagta actgtaggtc tgtcatttgg ttgccgcatc tttaaggact tgctcgtgcg   20340
tctgctccac ctgcttaacc agccacttga atgttacgtt aagccgcttt gacagctctg   20400
tagggattac tgtggtcttc accagaccct tgccgttgtg ttccgttacg gtcacgattt   20460
gagtcccacc attaacgccc gtctgcttgt gtgcgaattt cataactctc tcctgttaag   20520
cgaatgcaaa gtctgaagac aagatgtcct cgatattcag tttgcctttc ttcggaagct   20580
caggcaactt gtcgcgctga ctctcgtgaa gctggtattc gaactgctcg tagaagtcaa   20640
gcagaacatc gttgtcgcgg taggtctcga ccatcgtctc acggacacca cggaacagat   20700
actcagcatc agcagggatg gtcccgaagc tatcgtgaat cactgcgaac gacatcacgc   20760
catacttgcg gtgcgtgtgg actacagtct tgcggaggtg gctgccatct tgtgagtgga   20820
cgaagttcgg gctaatgcct gactcctgct tgtgcttgtc cagctctttc ttcgtacctc   20880
tgttgacggt aggctgaaga ttgaatgacc ctaagaacat caggttcaga cgagtggtat   20940
ccttcttgcg gtattcctgc cagaccggga accatcagg tgttacccag tgtaccggaa    21000
ggcaaggctt caggatttct ccagtcttct tgtccttcac ttcagcagcc agcagcttgg   21060
cagcaccttg aagccacttc atagcgtcaa ccgcagcaac tacggtcaca ctcaccgctt   21120
cccaaatcat cttagccatg aagcgagacg cttggcttgg ctcagtgaac atagcgccag   21180
```

```
accctgagtc aatcgctggc atcactatgt cctcgtatac ttggtctgcg aatccgtact    21240
ctttcgaccc gtaggccaga gtcatgaccg aacgcttagt aaccttgcgt gacataccgt    21300
aagtcaacca ctgacgggcc agctctcgtg tccccagctt gagacgctcg gtaatctcac    21360
cagttttctt gtcctcgtga gtcaccatct cgttatccgt accgttaacc agcaggactt    21420
tgagttcctc ctcaatgcgg tcggacacga tgcggtagat gtcttggacc ttaccggatg    21480
gcgtcaggtt tactgcatgt ccaccgatgt ggtcacgaag catcgcgctg aagtgctgaa    21540
tcccagagca ggacccatcg aacgctatcg gtagcgagca ggagtaagac aggccgtgat    21600
gcattactcc agcatactcg aagcagaacg cgaggaagca gaacggggag tctaacttgc    21660
cccaccactc aatgctatcc atcggtgcct tagcagtagc cataatgttg tcgtggttgt    21720
cttccaccca cttgatgcgc tcctcgaagg tgactttatc gacacccgca cagtttgcac    21780
catggacctt cagccatttg aaaccttcag caccaataga cttaccgact gccagagtca    21840
ggagacccctt ctgcatgtcg ttaccctgag ggttgaacat cggtacagcg tagacgcgac    21900
cgcgccagtc catgttgtat gggaaccaga tggccttaaa ctgagaaaac ttgttcgctt    21960
ggttaacgat aaagctcagt gacaacctgc gtgactgtcg ggccttctcg cgtcgataga    22020
taccagcagc agccttcttc catgccttga gttcctcctc agtctcaccc gcatagtcct    22080
caggcttcag tggctccatt tgagggatgt cgtcaatagg cgtattgttc agcttctcga    22140
ccatgttcac cacgtccagt accttcttgt tcactttcca aggcgtattc tggatgatgt    22200
taacagcgtc atatacttca ggcatgtaca cgtcttcgta acgtgccacc gcagacttag    22260
accctaagcg aatcagtggc aatggtctgc gacctttggc ccagtaccca ccgcctacga    22320
caccagtcca cggcttaggc ggaacgacgc aaggttggta gactggagcg atacccgcaa    22380
gactgaagcc acgttgtgcc atcttcttga cccagaagtc tgacaggtgg accatctcaa    22440
cgtcagtcgc tgcattaccg gcaccgtaac gcttaagctc gaccagttgt gttgactgga    22500
tgacaatctc aagcatctta attccaacgt ggacagcctc ggtcggactc caagttcccc    22560
acgcatcttc cagttgacct tgctcaagca ttgaggtctc aaccgcttgc atgtaggctt    22620
tcttgtagga tatccctgct cgcttgttca ggttatcagc tatcgccttt ttgaagtgct    22680
ccttctcctg atcacggatt ctaccgaagc gtatttcatc ctcaattgtg cgacctatcg    22740
cggatgccat aggtgtaatc ggtatcccctt caggcttgac cagcttggat aggatgacct    22800
ttagtatgat aaccgcagca gactcacagg agatgcgcag agagcgatcc ttgacggcct    22860
tctcttcagt gctcaacatg gtgaacgcta cgctaggacg agagattgac agcttcccgt    22920
ctggaccttc atgccactcc ttgactgctt gcgcaatctt agggaccaga gtctgcatca    22980
aaggcttggc gacctgattg tctgccagtt ccccgcgctc ggtctggcgc tcaaggttct    23040
tgatgaaacg tcgctcacct tcagtgtatg cctcatgctc aagctgaagt tgtttgactg    23100
caaggtcttg cccgtagtgg tcagccagca ggttaaacgg ctcaatggcg ttcgacacat    23160
cagagaagtc gtgtttgtca atagagatga cgctcatact taaagtcctt gttattagtc    23220
tttcacttaa agtctctttg gtctttcact tggagtctta gaccttgagt cctatagtga    23280
tagttaagtc agaattactt taatatcagt gggttagcgt gaagattact gaagtcacca    23340
tgagtcgtgt gcttgatggt tgaccgttgg tctatcgcct tccagcctga gaccagaagt    23400
ttaccgtcgt cggtgattgg ttgttcacca tacgccagac acatcagctc agacttatgg    23460
ccctctgccc ggagtcgtgc ctgtagcaca cggtcacgct cctcctgttg acgtgcggag    23520
tgacttgacg ttccgtggcg ataccctgta gccagtaggc ttaacatgtt catatctgcg    23580
```

```
tccatagagt gtaccagatt aatcccgtaa gacttgttca ttacagtttg ctcccaagtg   23640
ttgctatatc ccagacgttc gccaagttgc gcatgaatcg tccgttaggt tgacgtacag   23700
tccagcgacc catacgtaca tagttgaatt tgtagacttt acgcgccttg ttaatgtctc   23760
tcaccagcac gtaggcgata agtccatagc ctatgactat caatagtgcg atactcatag   23820
tgatttccgt ttaatacaat cgtatatacc ataacctatc atccagataa ctggcgctag   23880
gcatacccag taaccgatgt tcatagttaa ctcctatcaa tgtaagtgat aatcttcgag   23940
gccacctatc agtcgatgac ctctcgtcta tcactcagct attgcgttca tggttacacc   24000
tccaccgcta cagtggtcat cttgcttaca gtcagcccac cagcaagctc aaccgcatag   24060
cgtatagcct cctctttgga cttgaagtcc tttcctgcaa ggtgataaat gtcgcctgtt   24120
attaccttag aaggcctgcg acttaccgca atagcgtttt tcatggtaag ctcaccccgg   24180
ctatactgag taaaccagcg cttcaccgaa ctcgtcccca ccccgaactt tttggctgtt   24240
tccgtcaccc tatccatagc tccctcaggc agagaggtgt agtagttaac aacgttgagt   24300
ttaaatgcta ccgagaatac attgcgagct ttagcagtca ttattctttc cttctgtagt   24360
tgtaaagtgg taatcactca ggccaccatg tagatgacct gtagtttaac actcagtacc   24420
cgcctgtcag tgttatggtc agactttggt gattagctac gtagcaagca ccacgcttca   24480
tcatctcgta gcacccatcg tagaacgcct gttcactgct ataagttatc tggtacatgt   24540
tacttatcct catcgtgtag actatcgtga atacgtttgc ggccctcata daccgctttc   24600
aggtgacgca tagtcgcatc gtggtttaac tgcccggtct tgaccataat ccgggcgttg   24660
gtgacgtgat gctggcagag accgtaagtt aacatcactc gcagtcctcc tcagcagcct   24720
caaaccagac cacatccgag ctattagaca cgtcattata cagtgcctca tagatgcggg   24780
cttgtagtat acgcgttacg tccttggtct caggcatcag cccagagtct tcgaactcaa   24840
ggtcaatacc atcagcagcc atcaccgtga aaatctcgtg gtaatagagc ggaaccatat   24900
cgtctacgac ttcatgcagc gcatcgtggt aatcatcgcc ttcagctatt tcgtcatact   24960
gaatgcgctc gttaaatgct tcaacagttg cagccagcag ctcatagtat gcgttagcgt   25020
tacgttccat agttatatcc tctcaaaagt tgtttgtgta tgttagtgac catcagtcag   25080
ggccttcagg tgtagactca aagaccctgt agttaatcac tatcggcgca cattaagagt   25140
ttatccagat tgttaaagag cattcccttc agtcagatga cttcaggtag accatttcag   25200
tgttggtcgt caccgttgtt tcgatgtggt acagcttaca tcttatcgtt actgcttgtc   25260
aactactttc tgtcatctgc ctgttgttcg tatgacttac caggctgtct acttgaccgg   25320
gatgacccgg cgtcttcact atccggttgt tgccgtgtcg tgttgacgga agctattaag   25380
ccatagtcta gacctatagt caataggcaa tcttaaataa tattgattaa gctatcgtcg   25440
gccccatagt gactaagagg atagtctttg actaacatgt cttagacctt aagtctatag   25500
ctttgtgtct attagactgt aggtctttga ctgtaggtaa tggctttacc gatggtcggt   25560
gactgtaggt tgtaggactg taggttgttg agacctatgg ttatacagat agagactcgg   25620
agacaaccaa tagtcccaac ctatcgtcct gacctccagc catagcctca acctatcgtt   25680
gacctgaagt cttgaccatc ggtccaacct tatgatagac tggggtaggg cctttggtct   25740
ggacttaaag agggcctatg gggagacttg aggttcttga actgtgagat gtggtttcaa   25800
acttttggtc caaaactcat cgtcactact gtaggcctca gccactgtag gtcaaggacc   25860
gtaggtcagg cgacactagg atagaccaat aagtaggatg accctaagtg agcttctatt   25920
```

```
aaggtgttac ctaaagtcct tgactacagt agctaaggtc agtagagtga gtctttatcc   25980
acgtactgac cttaggtctt ccgctcatga atcgttacca tgattgcgtt aattacactg   26040
agagaccaga gagcatacga gagtctcgat ccacccgacc cactgacttc cagcagtaac   26100
gccagcagca agtagaacag cagcaagaaa cctgtatgta gctcgattgg tcgccagagc   26160
tttaagtaca gctttggtct ttgccatatg ctacatacct cctgtatcta tggtcggtga   26220
ctatatgtat tggagggatt atgattaata tcaccctcct tcaatcggtg caagccttag   26280
gtaagaactt gagtctgcct cctaaggtct tgcataaagt ctgcatatgt atattcacta   26340
cagtaatact ataagtaacc gggggtcttc cctatagtga tagttaagtc caaactcctt   26400
gtaaaacagt aggttagact ggtagtaact ataggttact aaccgcgtat tcatgcagct   26460
ttcacctata gttattcatt cagctagtgg aacgtaacgt atgaccctag tcctagctcg   26520
tcgtccgtat cgtgagttac ccggaccccca ttgtcccaga actcggtgtg gatggactcg   26580
aagcctttcc gtgggttctc catctgttcc tccagccact cctcagtgac ttcacgttct   26640
cctttgttgg catccttagc catcgactca acgaagaact gtacaccgat agccagtgca   26700
tcaagtcggt catcgtgtgc caaggctcca cgttcacgag agatacgggt catctggtag   26760
aagagagagt agatagggtt acgcacacca tccttgtcag aggctgtctg gtagtcttgg   26820
acgatagcag cagcgttgac gataagtcgg tgagacccca tgataggctc tagaacgtca   26880
cagatgcgta gttcttctg accccttactc ttcacttcag ttacagccgc aggatggata   26940
cgggccgcta caggcttgaa tagctcaagg tacataccat caccgaagtt accctcaatg   27000
acgtattcgt tgaccttcca cttacggcca atcttagcca gagcttccag cgtagagcct   27060
tcataaccac cacgcatgcc acccacttcc atagcgaaga tgtagccgtt gagctggtac   27120
agtaccgcat agccagtttc atccttacca cgaccactag ggtcaatgac cagaatcttc   27180
tgggtgtatg agctgaaggc agaacctaca gtctgatacg tgtggtacga gtcacccatg   27240
agtccaacgt taggaacatc ctcacgcttg ttctgagggt tcggcaacca ttggtagacc   27300
attgggctag acgctgggtc caagtctgct acgataaggt cacggagctt cagagggtac   27360
ttctctgcat cactcaggtt agggttaagc atgaactgta gcgcgaagcc agctttaccg   27420
taagatagct cacgttcctt aaggtccgta tcatcgaagc gtacttcatc agtcggacgc   27480
cagtagaagg actcagggtc ctcttccagc tctgcttgaa gcataggagc cagacggtcg   27540
ccgtaagact gccagtcctt cttatcgcgt ggataacgag ctggccagat agtagtggtg   27600
tacccacgac cttccagctc acgatacaag gtcatctcgt tctgaggagt acccagataa   27660
atgattgtac ctcccggctt caggatagca tcaaactctt tcacaagctc tgacagacgg   27720
tctcgtgcag cctgagtcgc tgagttgtta ggaacctcca cgtcatcggc aatcaggatg   27780
tcagcacgac taccagtcaa ctgaccagtg ataccaacag acttaaccga aggtgagtgg   27840
tctggctttg ctggcccaac gtcgaagcta ataaccgcat ctcgctgtcc ctgcttaggt   27900
ttgagttcct gaagctgagg catgaggtcg atgattcgct tgatgaatat ggagttagca   27960
tcggctcgtt cctttgaggc cgacacaatc atgaacttca agtctgggtt gttccatagc   28020
ttccagacca cgaaaccaca ggtcagaaac gatttgccaa taccacggaa cgcctgaagg   28080
atgaagcggc gattatcccc agcagccagc ttcttacaca tatctatctg gcagcgggtt   28140
ggaacaggaa gacttagtgc tttccagaga acgaagatga agaacacgaa gtcgtccctc   28200
atcctttggg tcatttctgc ctgtctttca gctggtgttt tcttagacat atagtccctc   28260
caatattagg tccactttgc agtaatcact taacaccttg gagcctcctt attgtgtcct   28320
```

```
gaagcgcctt ctccttaagg tctgcctcct gagttattcg gataagactt ttagaagttt    28380
ctgggtgtag ttcgactctg ccattaggga agcatcgact gacatctgac tcggtgagac    28440
ctgaggtgtt gactcggacg cgcagccgct tgttatcgcg gttaaggtca gcaataatcc    28500
tatcagtaga gccttccagc gcggacatct tgtcttgcca ctcggctgac actttgtcga    28560
gttcaccttg gacagcagcc cgttgattct ctcgtgcctc aagtttcgtg atgtactcat    28620
tgtttacctt cgcctcccac ttattgtctg ccacccagta gcctgaacag aacaggagtc    28680
ctgcaaccag ccaaggggcg catctacgta aaagttcgag catagttgcc ctcctcattt    28740
ctcagaatcc acgtagcgtc gctactcgta gtatgtatta accataaagg ccactacaca    28800
tagtaatgac cttgagtcta acacttattg aacaccatac ccggtgtcat tatcctcagt    28860
cgctgaaagc accttatcgt actctgcgtt cagggcctcc atatcagcca gcgtcttctc    28920
gtccacagac accttgctta acacaaagtt gtgacgagca agcagcttct caatggcgtt    28980
gtagagctga ggtgaacgct tagagtcatc ccgcaggtct tgcaacatga gtcgagcacg    29040
ttcagtatca agcatcaata ggaacttctc taagtccatc tgcgtcatgt tttaccacct    29100
cctttaatcg ttttgtagac tagcacacca atctggacaa cggtgtacgc gatagctgca    29160
acgtagaacc attcgttcag tgtaagtccg aagaagaacc gactggcacc atcagccgca    29220
gcggtcccta cgataggaga ggctttaagg acctcattct tgaagtctaa ctcaatcata    29280
aaacctccag tttaaagcgg gtcgtccgtg acccaaagtt gttaccataa gttggtcagc    29340
gtgtagttag cctttacctc cacaaccttc gacgattcaa taccttctga tgatatacaa    29400
accatccgaa gcgggttttc ctttatatta cggatgttac cgttcccgat atagctgctt    29460
ttatagccga agttgggtga ggtctgattt gaacagtacc cctgtcgcta gctgccccga    29520
taaacacatc ataaccagtt gaagcattaa aatcagagaa gaggcttaca ggggcgctat    29580
tttgtgctac tggtacagct gacgatgttc cataccgctt caatatgcca ggtgtgacag    29640
cataggactt accatcccctt ctgcatacaa tatccaagtc aaacgtgtaa ccatcaaacc    29700
cgaactgtgt agcatcttgg aaaaacttca ttacttcagc ggtagaacct ccagccggag    29760
caacgtaatt gaagccagag aaagtcattc gggtaaaacg gttgtctcgg tcaacagtat    29820
caaatgtctt atcaatctta aggctactaa gcccatatac cccgttcaaa attattgggt    29880
tttgggcacg agtgttcata ctaatatcca gcttaggagc attatataaa tctatgcgct    29940
cccctacagc cccagagcga tcggcaatgt taacagcaat agaaaaagtg gtattgtttc    30000
cttcaatttt gatggtggag cgtttatctg cattaattga aatggcaggg gatgcctcag    30060
ctgttgacat tcctgtaatc tccaatgctt gcacatactt agtgatgtat atctttgcct    30120
cttcactata gttacctgcc aaaacgttg cctggctgtc accaattctt atctcacctg    30180
tttcaattgt acttgaaatt actgacgtcc caacaatggg aacttcaacc ttagtcccta    30240
acggaacgga agatgtcatt gcacgatcaa gtgtcaacac attcccagaa attgctgtga    30300
tacggcgtgt ttctacccca ccagtagagt tggtgaatgc aatttcaaac cagatatcga    30360
accctgctgc atcagcaacc gtaacagtag tgtctccaat atttgccgct gagttaagtg    30420
tcgtgctcat tccttcaata gaaaccgtac actgcctggt actcccgccg atatagccca    30480
tcagttttat tgagttattc cggacgcgaa caccgtactt tgtcgaagtt gcaccgtttt    30540
ttgttccctg cgagtgccca taccaataca tggcaagatg taaaagatcg tagttgctga    30600
tacggtggtt gattgattta ttcttaacgg tagcgtaagg cgctgtgtaa atagctctcc    30660
```

```
cggctgctga tgctcctttt tcccctactc cgccattaac agtgaaacct tcgacggttt    30720
gatgccaatg gagacggtct ctgctcctat cgcgcggatc aattccaaca tggtgcagtg    30780
aaatatcaga tgatgttgac atgattattg ttgcgtcatt tccagccccg gaaaaagtaa    30840
atcctctgcg atcaacatca aggttgattg tatttgatag atagcttccg gaagggaatg    30900
ataacttaga tattatactg ttagcccttg caactctgtt tgcttcatct actgctgcag    30960
agttttcatc tggtcttgc cctccaaaac caaactccgc aaaacccatc ctctctctta    31020
caattaagtt ggcattaaaa ccaccagcta tggggatgga gtatgttgta ttatcttgtg    31080
ttgttgatat taaccaatct gattcagatt ttattccatg tttgttttta tatgttttta    31140
cagtcatccc ttcactgaat acggcaccat ccctgatgg caggattcca gacactaaat    31200
ctgaaacact attaaatgct atagttgtat ttttagtgac ccataatcta aagaagcat    31260 caccaacact aacccacgca cccagcccaa taccaccaga tgattcagga gttgaaccag    31320
caggaacgtt ctttggaagc gtgccatccc agcggtaata agcaccatcc tcttcccata    31380
gcaggacctc gttccatgtt gtaacgttga agcctttctc gaaggagcga cgggtaatat    31440
agccaattag accagctgcc ttgatactcg cagcgattcg tcgtgcttcg tcctcgctat    31500
ccttagcgtt gccagcagag ataccagcag catcggcatg ttccttcgct aagtcaacag    31560
tttggtctcg accttcttct gcaatatgga tagcctgaag ctctgcattg gtcaggtcac    31620
tagctgtcaa cactgagcca ttcctgaagt ctaccactaa gtcagttcca gtctgacgat    31680
gaatacgaac gatgtcaaaa cctgattggt caaccaacat ctcaatcatc gttggattaa    31740
ggaatcggta atctcgacca gcttccagta cacggctcag ggcagggtta gagctgttca    31800
ccagcgtaac aacaacaaac gttctggcta ggtagtcgaa ctcaatcctg tactgagtgt    31860
ttcctgaagg gaattgtgta atcgtagaca ttatgcctcc tttgtgattt aaaggagacc    31920
tatggtagcg cctcctttgt gatttaaacg tagacctatg gtagcgcctc ccgtttccta    31980
tagtgatagt ttagtccttg atgtggattc cttgctcctc aaacgttcca agcaacagct    32040
tctgggtaat ggggtcgttc ggaaccagtt cacggaacgt attatacatc ccggtcatgt    32100
agtcacgctc attgacacga gtatcagcct tgaggtagcc agccaagttg taagccgaag    32160
cgccaacgtt agcagcatat ccgaaagccg gaacctgctc caagaagtta ccaacgacat    32220
tcatcacagg gtcacttgta gctgcaccat acgcgatggc acgttcaggc ttctctgtag    32280
gcgaacgagg taggatagac gaacggagca tcttagtgtc ctcatacccac gcgataccc    32340 caagaatgtt agctaccccca gtggtccac caagatgtga actacgtgat agagctgcat    32400
atccaatcat cgtcgggtcc agagcttgct tgaggtagtc acggtctcga ccatcctgca    32460
tagcgtaagc cttgacatgc gcctgagcca tgtagtagat accagcaaga cccatagaga    32520
tcacagtgga cagagcagcg tccatcgctc ggttgttctt cgtggcgtta tagaaggttc    32580
gcatggtacg tccattgatg gacttgatga cgaagttctt aaactgaagg acagtcttag    32640
cgagaggacc ataagccttg gcgtccatgt ttgacagctt gtggggccgg agtaacgttt    32700
cgtcagcgat ggtgtcaccc atacgccaca ggtccatagc ccttgggtcc tgactaaacg    32760
ccttcttatc cttgatggtg tacttcccgt ctggaccacg agtcactgac tcccggatta    32820
gggacttaat gccttttccac tgctcgtcag atataccagc ggtcttaagc cagcggtcat    32880
cgaacttacg cttactacca gtcaggctat gctccacgat gtcagacagg aagccttgac    32940
gtccagcatc taacaggtag ttggtcgtac cgttgaggac tttagtgaac ggagaacgta    33000
ctgcaagttc accggtgtaa tacttggcag tccccagagc tgtagctgta ccacgcccga    33060
```

```
ggtcactgta agaccgcaga cggtcaatga catcctgttt agacggacgg attgagtcat    33120
ccagttcctt accgaagatc acattatgca ggtccttaat ctccgaggct cccatcttct    33180
tgttacggaa ggctaggtca cggaacatag ggactccatg tagcattgca cgaacgttac    33240
cgcgagccag cataccacca atctccgtta agttctgaac acccatgtag gcattcttag    33300
cgaagaacga taggtctgtc attgtgcgca tcacggtagc gaaggctgca tcatcagcac    33360
catcacgtcg agcacgacca gttagaatct tcaaggtgtc acgtaaggtg gatacttcac    33420
ctttcaactt accgtcatcc ccagccttgt tcatcatggt ctcaaccaag tccttcatgt    33480
ccttcgtggt tttgcctgta ccagccatga tagcaatatc gccattaact cgacggttgt    33540
aggccgggac aatcttgtcc atgtcccact cacgcaggtt gttgacactg aaggtctgac    33600
cattaggtag gacgattgac atatcgctat cgaacaggtt acgagcctca aggaagctgt    33660
tgttctccag accaaccaga ccgttgatgt tctcttccat tacggatgaa cgttcgaact    33720
gctcggtgtg agagataccg taagccttat cgttggcgta cttatcgacc gcagcagcaa    33780
gtccctctgg agtcaacgta gggtcagcct ctaagagtgc ctcgtccacg cgtttcttga    33840
cttcaggtcg agacgcatag ctggtcaacc atgacttctt gatggcctcc tgtagcgcct    33900
ctggactccc aagctccttg atgtacagct ccttcatctg tttgctgtac acatgaggga    33960
cgtaggttcc cttgaagcgg ctacccggaa agatagactg agcgtctgtc cgaccaaaca    34020
tagctggatt ctccatcatc tcacgcttgg cgtcaaactg gttcttcagt aggtcataga    34080
ctttcagttc tcccggagtc agttcagcct tcaggtttcc gctaccatct tcgatagcca    34140
tagacacacg ctggtagatg tcctgacgga atgcgccaga gtctcgccag aatgctgtct    34200
ggaagtacgg gtcttttagt gcctcagtaa tcgcatcgtc gatgtcgttg tagaaccgat    34260
ggtccacagc acgaagtctc tcgaatacgt ctgacgcagt ggtcccgatt ttacctgatg    34320
cccctgactg cataccagtc ggtgagcgca ctaagtcagc agctactcca cgaatctcag    34380
ggttctcaga ccgaagcagc ttcaggccaa tctcggtaag tccaccaagg ttcacaccag    34440
cagcggcacg ttcaggctca atcacttcat caaagacctg acgtgtctta gggttcagag    34500
ggttctcacc aatcaggatt gaaccatctt caagtcgtac actacccggc tcattcggaa    34560
cgtcagcgaa cttaactcct tgatgactaa aggtctgctc accttcctga cagggagac    34620
gagacaggtc ctgaccatca acgttacgag cggtctcacg ggcttccaga cgtgtagctg    34680
gaccagcgaa ctcattagtg ttgcgaccta aggctctacc taagccatca gcgatagcag    34740
tcatacctgc accgaataga gcaccaccaa ggatagcttc agccacatga gcatcaccac    34800
cagccactga ggtacgggca acctcagaca caccagatag tgctccagct tgggcagcca    34860
ctgtgaacat cttgttgacc agcttgccgc ctttacccac ctgtccagcg ataggaacgt    34920
aggtcagcgg gtctacacca gcaccaatca caccagcagc taactgagca ccaatcccgg    34980
ccttggcctt ctcttggtcc aacttctggt tctcaagcgc caagttaata agctcggtca    35040
ggttctgagg agaaccacca gtaatgactc cataatactg aggcaggacc ccagagttac    35100
gaatctggtc cagctcctcg cgagtccact tatggttgtt ccatctggta gggttgaaca    35160
catcaccaat gacatcaagt gagtcctcgg tctgaccagc gcggatagcc acgccgacaa    35220
gagagttttt cacttcagct tctgtagcag caccgaaacc gaaccacgta gagcggtctt    35280
ctcgttcctg catggtctcg ccagtagcct tatagaacat ctcaccgaac gattcgttgg    35340
gagcttcagg ttcttgaccc tcaatgttta gaccagcagc ggtcggaagg ttctcaccca    35400
```

```
gagctacttt aggtttagcc ttgaggcctt ccgtgagtgc gtcaaatacg ttagcgctta   35460
ctggtggagt ctttggggtg atgcccccg caccacttaa ggcgcgagag actcctagct   35520
tgtagacctc agggtcatac cgggaaccag tctcatggta gccgatagcc tcagacagag   35580
aggcgaggac atcaggatta gtcaagtcaa tgctttgggt cgctggaatg ccagtagcag   35640
ccacaaccga gtcgatgtag gactgagtgt cgttctcgct gggtggtgcc catcggttga   35700
taatcttctc gattgagtcg tagccctgtc gaccgtacga catcaggttc ttagccagag   35760
cgcggacgcc agagtcagga gtgtcgaacg ttacgaaaga cccatcgtct cctgtagctc   35820
cttcccactg gtctttggaa acacgaatgt tcccgatgtt attgttgcga ataccacgag   35880
tcgccattgt tattactcct taccgattaa ggtgtttgcg atactctcca gcgagacatc   35940
actgtacaga ccgccgcgtt tctggatgtt accttcacgc tcggctcgac gtttatcacc   36000
agccgattta gtctcgacaa tgcgagagcg ggtgttggct ttacgttcag cttcagcgta   36060
ggctttatcc tcagcttgtt tctgctgttc acggtacagt ttacccacca gttctttatc   36120
gtatcgaatg cgtagggttc cgttagcgct ctgcaggaag accgagccgt tctgctcaac   36180
tacagagagc tgagagttca cgacccaagg gttagccttg acgagcagct tgcgagctgt   36240
gtcgatgatg tctcgaccaa ccttccaaga ctcagggtta tccccgacca taagttgatg   36300
gcgggacacc atgccgattg acttaccatc ctgaccatca tcggtgaaag tcacggtgtg   36360
ttcattcaac cacttctggg tattctgagt ggctccgtca gcgttacctg tcctgtagta   36420
ccatgagtcc catactttc gtgcaatcat cttcaattca gtcggtatcc ttgagagttg   36480
agtctccttt gagtcattcg tcagctctct ccactccttg tctgcctcac ttcgcatctc   36540
acgcgataaa cttgcagctt gcttatcagc ttcaatcagc gtctgagggt ccagacctat   36600
cttgtcaatc tgctcgaaag tcgtgaacaa ttgggcctgc tcagggtaga ggaccgcgaa   36660
gctggaaggg tcctgagtgt agaccttacg cagagactcg aagcgtttca tcctgtctgg   36720
gtcgtactgt ccacggatga cagcagcttg ccactcacca gcagcgtcct gaatcagcgt   36780
ctggaaggca ttacggaacg gaccattgtt agtgtcagct ctcaacaatg ccaccttctg   36840
agcgtcctta gcagcctcag ggatgtccat ctggtcaatc tgctgtagct tggcagacgc   36900
atagttgttc atgtctgaac gcttgaactc tcctgtggct tcagagaccg gaaggtcctc   36960
atagttggtg gacacgtttt ctccagccag acgtcgctga tacacttggt cgatgaccag   37020
ttgcttgttc tgggtctgga ttaacttagc gttctccttt gcctgttcag cagacttacg   37080
ctttaccgct tccagtaagc tggcttcggc attaataagc atctgacgct gaggtgtgag   37140
ttcttcaccc ggttgaagca ggttgttctg ctccttgagt ttctgaatct gggccagacc   37200
gatggttggg tcatcctgaa gaatagcaga ctgaacgccg agtgctaagt cttcctgata   37260
cttagccacc agtttatact cagtaccttg ggcctcaacc atagcagcat gaagacgtc    37320 aggtcctaca atctcttcga tggtagcgtc aacaccatta agggtgatac gctcgccacg   37380
gacttgctgt aggaagtttg agcctcctga cttctggatt gcgtcacgta ccgtctgggt   37440
gattacctct cgtgctctct ggtctgaagg tatagcagca gtcgtcaggc catcccgaat   37500
```

```
                                                              -continued
gtaggccatg aaggtctttc cagactcagg cgaacgcatc aggtccccat cgttaaggaa  37560
cgagttcatc tcaatacgag tgttcaacat tgcggtctct tcagactgct tgctgaaata  37620
cttattgaat gacccgtaga tagcgatgtt tcggtccgtg atattatcgt taaatccacg  37680
ctggaagaac tcgtcggtag ggttaatacc agcctcttca gcataagact tagctgcgtc  37740
ttgaagtcgc tggtggcgat attcttccat ttcctgacgt gtgcggaact caccgttctg  37800
aatcttaacg ttaatctcgt cgtctacagc aaaggcagca ttacgaccag tcttgactcg  37860
aagtgcttcc atagcgtaag ggtcatcctg atacagcaat gtgccgttct ggatagcctc  37920
acgtctctgc tgaggtgtca acttacggat aatctcgtta gaccgctcgt cagctctggt  37980
cttctcatcg tccttgaact gcttgtacaa tcctgtccca gactcaacga agttagtcaa  38040
tgcacgagcc agcccggagt ccccagtcgg agcctgaacg ttggctgctt gatagttgac  38100
ggcgatagtt ttacccggcg ctctgccacg acccatagtc cgattagcca gagctgattc  38160
aatattacta gccattagtc ctcctcttag ctatgacctg taggtgtgcc tttagcagca  38220
ctaatcggtg cagcaccacc agagcttgat gccccagaga ttgacttacc agcagcgtac  38280
ccctgcatcc cggcgcttgc aacattaagt gcatgagcca gtgggctggt cttgatgatt  38340
ttaccctgac cacggatagc agacttggtg ttctcaatgt tggcgatacg gttcccgaag  38400
atagccgcat agtcgcggtt gtaactttcg gtaatccctg ctcgctcctt gactgtatct  38460
ccttcgacct gacgttcaat cctgtccata gagttaccett ccagaccgga ctcagccacc  38520
gcagctcgga ccatacctg attgcgtata ccgttgagcg tggtctctgt cagttcagcc  38580
atctgctgct ccttcaggtc tcgctcctgc atcctcaggt tggcgtcaga atagttcatc  38640
tgcttaacca tttcctgagc ctgtcggttc tgagcgtcaa ttgctgcacc ttcggccttg  38700
gcctgctggg atgcggacat agtggccccg gctacagcca tgatgcccat ggcgatactt  38760
acgggttcac acatacgtcc tccttagaga tagtgaataa ttgaaaacgc tcaccagtta  38820
ccgggctgat agtccaatca tcatggaact tagccccaag caacttcaag aatttaatgt  38880
gagacttatt gcctgaccac acgtagttcc agatggtccc gtattggtct aacattaagt  38940
ccctgtactc agagatacgc tttacgaact ctcgcttctc tttaggtctc agcttataga  39000
caagaccgga agtcaagaac catacgttat ccccttggtt tccaccatag gcaaacactt  39060
cgcctacacc gttcgttaaa accacagatg acggggataa atgcttaagc agtctttcag  39120
atagacccac ggttgaccca tagtttgctt tgcattcatt aacatcatct gctgaaagat  39180
gccacagaaa gtagtggaca tctggttccg tagccttgcg aatatacata aagtctcctt  39240
ataaccttaa gggcctatag tccctatagt gatagttaag gtaaatctat aggccattca  39300
ataagttaaa cggaacgagc tttcttagcg tatgacgcct cccagccaca cccaacgatt  39360
gacactgggg taggatagtc ggactctaag gttagactcg tggttaatgc gttaccattc  39420
atagcgaagc gatactgacc atccccaatg ttggtagtcc cgatggtttg ctgaccaagg  39480
gtgtacccat taaaggtgtt cacgaactcc cgctcaccgt ttctgacaat gagtctaaga  39540
gcaccagtgt ccttgtagtt gacccaagcc cgacgaagtt gtaggcgtcc agtgtcttca  39600
gactgagtgc cactttcg                                               39618
```